US012714319B2

(12) United States Patent
Rowland et al.

(10) Patent No.: US 12,714,319 B2
(45) **Date of Patent: *Aug. 25, 2026**

(54) PRESSURE SENSOR, ANCHOR, DELIVERY SYSTEM AND METHOD

(71) Applicant: Endotronix, Inc., Naperville, IL (US)

(72) Inventors: Harry D. Rowland, Plainfield, IL (US); Michael Nagy, Lombard, IL (US); Kevin MacDonald, Sacramento, CA (US); Alyssa Kurt, Lake Villa, IL (US); Andy Black, Johnsburg, IL (US); Andy Leopold, Hawthom Woods, IL (US)

(73) Assignee: ENDOTRONIX, INC., Lisle, IL (US)

( * ) Notice: Subject to any disclaimer, the term of this patent is extended or adjusted under 35 U.S.C. 154(b) by 1032 days.

This patent is subject to a terminal disclaimer.

(21) Appl. No.: 16/243,183

(22) Filed: Jan. 9, 2019

(65) Prior Publication Data

US 2019/0142285 A1 May 16, 2019

Related U.S. Application Data

(63) Continuation of application No. 14/428,551, filed as application No. PCT/US2013/059769 on Sep. 13, 2013, now Pat. No. 10,206,592.

(Continued)

(51) Int. Cl.
*A61B 5/0215* (2006.01)
*A61B 5/00* (2006.01)
(Continued)

(52) U.S. Cl.
CPC .......... *A61B 5/0215* (2013.01); *A61B 5/0022* (2013.01); *A61B 5/076* (2013.01);
(Continued)

(58) Field of Classification Search
CPC ..... A61B 5/0215; A61B 5/076; A61B 5/6851; A61B 5/6852; A61B 5/6876; A61B 5/6882; A61M 25/01; A61M 25/0662
See application file for complete search history.

(56) References Cited

U.S. PATENT DOCUMENTS 3,714,595 A 1/1973 Denenberg et al.
3,872,455 A 3/1975 Fuller et al.
(Continued)

FOREIGN PATENT DOCUMENTS

CN 1701464 11/2005
CN 101116322 1/2008
(Continued)

OTHER PUBLICATIONS

Extended European Search Report for application EP13850155.6, PCT/US2013/059769, dated Apr. 19, 2016, European Patent Office, Germany.

(Continued)

*Primary Examiner* — Puya Agahi
(74) *Attorney, Agent, or Firm* — McDonald Hopkins LLC

(57) ABSTRACT

An implant delivery system includes an implant, such as a wireless sensor, a first sheath, and a second sheath. The sheaths extend from a proximal end of the implant delivery system, and at least said first sheath extends to a distal end of said implant delivery system. The first sheath is positioned at least partially within said second sheath. The implant is connected to an exterior surface of the first sheath and positioned near an end of the second sheath. The first sheath and said second sheath are movable with respect to one another to deploy said implant to a desired location.

9 Claims, 11 Drawing Sheets

Related U.S. Application Data

(60) Provisional application No. 61/701,058, filed on Sep. 14, 2012.

(51) Int. Cl.
*A61B 5/07* (2006.01)
*A61M 25/01* (2006.01)
*A61M 25/06* (2006.01)

(52) U.S. Cl.
CPC .......... *A61B 5/6852* (2013.01); *A61B 5/6876* (2013.01); *A61B 5/6882* (2013.01); *A61M 25/0662* (2013.01); *A61B 2560/066* (2013.01); *A61M 25/01* (2013.01); *A61M 2025/0681* (2013.01)

(56) References Cited

U.S. PATENT DOCUMENTS 3,888,708 A 6/1975 Wise et al.
3,943,915 A 3/1976 Severson
4,023,562 A 5/1977 Hynecek et al.
4,026,276 A 5/1977 Chubbuck
4,037,324 A 7/1977 Andreasen
4,067,235 A 1/1978 Markland et al.
4,127,110 A 11/1978 Bullara
4,206,762 A 6/1980 Cosman
4,385,636 A 5/1983 Cosman
4,407,296 A 10/1983 Anderson
4,485,813 A 12/1984 Anderson et al.
4,511,858 A 4/1985 Charavit et al.
4,531,526 A 7/1985 Genest
4,543,955 A 10/1985 Schroeppel
4,567,459 A 1/1986 Folger et al.
4,644,420 A 2/1987 Buchan
4,815,472 A 3/1989 Wise et al.
4,881,410 A 11/1989 Wise et al.
4,953,387 A 9/1990 Johnson et al.
4,966,034 A 10/1990 Bock et al.
5,005,577 A 4/1991 Frenkel
5,006,819 A 4/1991 Buchan et al.
5,013,396 A 5/1991 Wise et al.
5,046,497 A 9/1991 Millar
5,055,838 A 10/1991 Wise et al.
5,058,581 A 10/1991 Silvian
5,059,543 A 10/1991 Wise et al.
5,108,420 A 4/1992 Marks
5,113,868 A 5/1992 Wise et al.
5,227,798 A 7/1993 Hildebrand
5,257,630 A 11/1993 Broitman et al.
5,262,127 A 11/1993 Wise et al.
5,282,827 A 2/1994 Kensey et al.
5,296,255 A 3/1994 Gland et al.
5,334,952 A 8/1994 Maddy et al.
5,343,064 A 8/1994 Spangler et al.
5,368,040 A 11/1994 Carney
5,377,524 A 1/1995 Wise et al.
5,411,551 A 5/1995 Winston et al.
5,417,235 A 5/1995 Wise et al.
5,487,760 A 1/1996 Villafana
5,510,276 A 4/1996 Diem et al.
5,564,434 A 10/1996 Halperin et al.
5,581,248 A 12/1996 Spillman, Jr. et al.
5,690,674 A 11/1997 Diaz
5,840,148 A 11/1998 Campbell
5,872,520 A 2/1999 Seifert et al.
5,873,835 A 2/1999 Hastings et al.
5,920,233 A 7/1999 Denny
5,938,602 A 8/1999 Lloyd
5,992,769 A 11/1999 Wise et al.
6,015,386 A 1/2000 Kensey et al.
6,025,725 A 2/2000 Gershenfeld et al.
6,109,113 A 8/2000 Chavan et al.
6,111,520 A 8/2000 Allen et al.
6,126,675 A 10/2000 Shchervinsky et al.
6,140,144 A 10/2000 Najafi et al.
6,174,322 B1 1/2001 Schneidt
6,190,400 B1 2/2001 Van De Moer et al.
6,206,835 B1 3/2001 Spillman, Jr. et al.
6,232,150 B1 5/2001 Lin et al.
6,278,379 B1 8/2001 Allen et al.
6,287,256 B1 9/2001 Park et al.
6,309,350 B1 10/2001 VanTassel et al.
6,331,163 B1 12/2001 Kaplan
6,338,284 B1 1/2002 Najafi et al.
6,359,444 B1 3/2002 Grimes
6,366,804 B1 4/2002 Mejia
6,438,408 B1 8/2002 Mulligan et al.
6,447,449 B1 9/2002 Fleischman et al.
6,454,720 B1 9/2002 Clerc et al.
6,459,253 B1 10/2002 Krusell
6,471,656 B1 10/2002 Shalman et al.
6,477,901 B1 11/2002 Tadigadapa et al.
6,499,354 B1 12/2002 Najafi et al.
6,570,457 B2 5/2003 Fischer
6,592,608 B2 7/2003 Fisher et al.
6,636,769 B2 10/2003 Govari et al.
6,645,143 B2 11/2003 VanTassel et al.
6,647,778 B2 11/2003 Sparks
6,658,300 B2 12/2003 Govari et al.
6,666,826 B2 12/2003 Salo et al.
6,667,725 B1 12/2003 Simons et al.
6,680,654 B2 1/2004 Fischer et al.
6,682,490 B2 1/2004 Roy et al.
6,699,186 B1 3/2004 Wolinsky et al.
6,713,828 B1 3/2004 Chavan et al.
6,749,622 B2 6/2004 McGuckin, Jr. et al.
6,764,446 B2 7/2004 Wolinsky et al.
6,779,406 B1 8/2004 Kuzina et al.
6,783,499 B2 8/2004 Schwartz
6,805,667 B2 10/2004 Christopherson et al.
6,817,983 B1 11/2004 Millar
6,824,521 B2 11/2004 Rich et al.
6,838,640 B2 1/2005 Wise et al.
6,844,213 B2 1/2005 Sparks
6,855,115 B2 2/2005 Fonseca et al.
6,890,300 B2 5/2005 Lloyd et al.
6,893,885 B2 5/2005 Lemmerhirt et al.
6,916,310 B2 7/2005 Sommerich
6,923,625 B2 8/2005 Sparks
6,926,670 B2 8/2005 Rich et al.
6,932,114 B2 8/2005 Sparks
6,935,010 B2 8/2005 Tadigadpa et al.
6,939,299 B1 9/2005 Peterson et al.
6,945,939 B2 9/2005 Turcott
6,959,608 B2 11/2005 Bly et al.
6,968,743 B2 11/2005 Rich et al.
6,970,742 B2 11/2005 Mann et al.
6,981,958 B1 1/2006 Gharib et al.
7,001,398 B2 2/2006 Carley et al.
7,004,015 B2 2/2006 Chang-Chien et al.
7,013,734 B2 3/2006 Zdeblick et al.
7,025,727 B2 4/2006 Brockway et al.
7,028,550 B2 4/2006 Zdeblick et al.
7,048,756 B2 5/2006 Eggers et al.
7,059,176 B2 6/2006 Sparks
7,059,195 B1 6/2006 Cook et al.
7,066,031 B2 6/2006 Zdeblick et al.
7,073,387 B2 7/2006 Zdeblick et al.
7,081,125 B2 7/2006 Edwards et al.
7,137,953 B2 11/2006 Figler et al.
7,146,861 B1 12/2006 Cook et al.
7,147,604 B1 12/2006 Allen et al.
7,149,587 B2 12/2006 Wardle et al.
7,162,926 B1 1/2007 Guziak et al.
7,174,212 B1 2/2007 Klehn et al.
7,191,013 B1 3/2007 Miranda et al.
7,192,001 B2 3/2007 Wise et al.
7,198,603 B2 4/2007 Penner et al.
7,211,048 B1 5/2007 Najafi et al.
7,228,735 B2 6/2007 Sparks et al.
7,245,117 B1 7/2007 Joy et al.
7,273,457 B2 9/2007 Penner
7,274,965 B1 9/2007 Karicheria et al.

(56) References Cited

U.S. PATENT DOCUMENTS 7,284,442 B2 10/2007 Fleischman et al.
7,290,454 B2 11/2007 Liu et al.
7,353,711 B2 4/2008 Hynes et al.
7,425,200 B2 9/2008 Brockway et al.
7,432,723 B2 10/2008 Ellis et al.
7,466,120 B2 12/2008 Miller et al.
7,483,805 B2 1/2009 Sparks et al.
7,498,799 B2 3/2009 Ellis et al.
7,550,978 B2 6/2009 Ellis et al.
7,574,792 B2 8/2009 O'Brien et al.
7,621,036 B2 11/2009 Cros
7,641,619 B2 1/2010 Penner
7,645,233 B2 1/2010 Tulkki et al.
7,647,831 B2 1/2010 Corcoran et al.
7,679,355 B2 3/2010 Allen et al.
7,686,762 B1 3/2010 Rich et al.
7,686,768 B2 3/2010 Bodecker et al.
7,839,153 B2 11/2010 Joy et al.
7,899,550 B1 3/2011 Doan et al.
7,932,732 B2 4/2011 Ellis et al.
7,936,174 B2 5/2011 Ellis et al.
7,973,540 B2 7/2011 Ellis et al.
8,014,865 B2 9/2011 Najafi et al.
8,021,307 B2 9/2011 White
8,103,361 B2 1/2012 Moser
8,104,358 B1 1/2012 Jia et al.
8,111,150 B2 2/2012 Miller et al.
8,118,748 B2 2/2012 Schugt et al.
8,118,749 B2 2/2012 White
8,154,389 B2 4/2012 Rowland et al.
8,159,348 B2 4/2012 Ellis
8,237,451 B2 8/2012 Ellis et al.
8,353,841 B2 1/2013 White
8,355,777 B2 1/2013 White
8,360,984 B2 1/2013 Yadav et al.
8,373,559 B2 2/2013 Mccain
8,424,388 B2 4/2013 Mattes et al.
8,432,265 B2 4/2013 Rowland et al.
8,493,187 B2 7/2013 Rowland et al.
8,512,252 B2 8/2013 Ludomirsky et al.
8,565,866 B2 10/2013 Hedberg et al.
8,665,086 B2 3/2014 Miller et al.
8,669,770 B2 3/2014 Cros
8,700,924 B2 4/2014 Mian et al.
8,852,099 B2 10/2014 Von Arx et al.
8,870,787 B2 10/2014 Yadav et al.
8,901,775 B2 12/2014 Armstrong et al.
9,265,428 B2 2/2016 O'Brien et al.
9,496,924 B2 11/2016 Aber et al.
9,498,130 B2 11/2016 Rich et al.
9,712,894 B2 7/2017 Iannotti et al.
9,839,732 B2 12/2017 Armstrong et al.
10,022,054 B2 7/2018 Najafi et al.
10,105,103 B2 10/2018 Winshtein et al.
10,143,388 B2 12/2018 Cros et al.
10,205,488 B2 2/2019 Hershko et al.
10,206,592 B2 2/2019 Rowland et al.
10,307,067 B1 6/2019 Xu
10,383,575 B2 8/2019 Najafi et al.
10,478,067 B2 11/2019 Najafi et al.
10,687,709 B2 6/2020 Najafi et al.
10,687,716 B2 6/2020 Goldshtein et al.
10,709,341 B2 7/2020 White et al.
10,874,349 B2 12/2020 Goldshtein et al.
10,874,479 B2 12/2020 Forsell
11,154,207 B2 10/2021 Campbell et al.
11,206,988 B2 12/2021 Goldshtein et al.
2001/0018598 A1* 8/2001 Cruise ................ A61B 17/0057 606/214
2002/0045921 A1 4/2002 Wolinsky et al.
2002/0072656 A1 6/2002 Vantassel et al.
2002/0111662 A1 8/2002 Iaizzo et al.
2002/0115920 A1 8/2002 Rich et al.
2002/0138009 A1 9/2002 Brockway et al.
2002/0151816 A1 10/2002 Rich et al.
2002/0156417 A1 10/2002 Rich et al.
2002/0177782 A1 11/2002 Penner
2002/0188207 A1 12/2002 Richter
2003/0062957 A1 4/2003 Terashima et al.
2003/0083718 A1 5/2003 Cox
2003/0125790 A1* 7/2003 Fastovsky ............ A61B 5/0215 606/108
2003/0135246 A1 7/2003 Mass et al.
2003/0136417 A1 7/2003 Fonseca et al.
2003/0139677 A1 7/2003 Fonseca et al.
2003/0139771 A1 7/2003 Fisher et al.
2003/0158584 A1 8/2003 Cates et al.
2003/0191496 A1 10/2003 Edwards et al.
2004/0024440 A1 2/2004 Cole
2004/0102806 A1 5/2004 Broome et al.
2004/0147969 A1 7/2004 Mann et al.
2004/0158138 A1 8/2004 Kilcoyne et al.
2004/0176672 A1 9/2004 Silver et al.
2004/0220637 A1 11/2004 Zdeblick et al.
2004/0255643 A1 12/2004 Wise et al.
2004/0260164 A1 12/2004 Kilcoyne et al.
2005/0013685 A1 1/2005 Ricketts et al.
2005/0015014 A1 1/2005 Fonseca et al.
2005/0043601 A1 2/2005 Kilcoyne et al.
2005/0049634 A1 3/2005 Chopra
2005/0080346 A1 4/2005 Gianchandani et al.
2005/0090719 A1 4/2005 Scheiner et al.
2005/0103114 A1 5/2005 Bly et al.
2005/0145187 A1 7/2005 Gray
2005/0154321 A1 7/2005 Wolinsky et al.
2005/0160825 A1 7/2005 Zdeblick et al.
2005/0160827 A1 7/2005 Zdeblick et al.
2005/0187482 A1 8/2005 O'Brien et al.
2005/0228308 A1 10/2005 Iddan et al.
2005/0273147 A1* 12/2005 Israel .............. A61M 25/09025 623/1.11
2005/0288596 A1 12/2005 Eigler et al.
2005/0288604 A1 12/2005 Eigler et al.
2005/0288722 A1 12/2005 Eigler et al.
2006/0004286 A1* 1/2006 Chang .................... A61B 90/16 606/198
2006/0041270 A1* 2/2006 Lenker .............. A61B 17/3439 606/198
2006/0041281 A1 2/2006 Von Arx et al.
2006/0047205 A1 3/2006 Ludomirsky et al.
2006/0052821 A1 3/2006 Abbot et al.
2006/0064036 A1 3/2006 Osborne et al.
2006/0064133 A1 3/2006 Von Arx et al.
2006/0064134 A1 3/2006 Mazar et al.
2006/0064142 A1 3/2006 Chavan et al.
2006/0064143 A1 3/2006 Von Arx et al.
2006/0085039 A1 4/2006 Hastings et al.
2006/0109188 A1 5/2006 Keda et al.
2006/0116590 A1 6/2006 Fayram et al.
2006/0122522 A1 6/2006 Chavan et al.
2006/0129050 A1 6/2006 Martinson et al.
2006/0135963 A1 6/2006 Kick et al.
2006/0161171 A1 7/2006 Schwartz
2006/0177956 A1 8/2006 O'Brien et al.
2006/0178583 A1 8/2006 Montegrande et al.
2006/0178695 A1 8/2006 Decant, Jr. et al.
2006/0196277 A1 9/2006 Allen et al.
2006/0206146 A1 9/2006 Tenerz
2006/0212047 A1 9/2006 Abbot et al.
2006/0217762 A1 9/2006 Meahs et al.
2006/0217763 A1 9/2006 Abbot et al.
2006/0217764 A1 9/2006 Abbot et al.
2006/0229488 A1 10/2006 Ayre et al.
2006/0241354 A1 10/2006 Allen
2006/0244465 A1 11/2006 Kroh et al.
2006/0247725 A1 11/2006 Gerber et al.
2006/0271078 A1 11/2006 Modesitt
2006/0287602 A1 12/2006 O'Brien et al.
2007/0007240 A1 1/2007 Wise et al.
2007/0016084 A1 1/2007 Denault
2007/0028698 A1 2/2007 Guziak et al.
2007/0032734 A1 2/2007 Najafi et al.
2007/0049980 A1 3/2007 Zielinski et al.
2007/0049984 A1 3/2007 Osypka

(56) References Cited

U.S. PATENT DOCUMENTS

2007/0060959 A1 3/2007 Salo et al.
2007/0073351 A1 3/2007 Zielinski et al.
2007/0088221 A1 4/2007 Stahmann
2007/0088388 A1 4/2007 Opolski et al.
2007/0088405 A1 4/2007 Jacobson
2007/0093720 A1 4/2007 Fischell et al.
2007/0096715 A1 5/2007 Joy et al.
2007/0100215 A1 5/2007 Powers et al.
2007/0106246 A1 5/2007 Modesitt
2007/0106328 A1 5/2007 Wardle et al.
2007/0106333 A1 5/2007 Fernandez
2007/0112358 A1 5/2007 Abbot et al.
2007/0118039 A1 5/2007 Bodecker et al.
2007/0149880 A1 6/2007 Willis
2007/0160748 A1 7/2007 Schugt et al.
2007/0163355 A1 7/2007 Nassar et al.
2007/0179583 A1 8/2007 Goetzinger et al.
2007/0208390 A1 9/2007 Von Arx et al.
2007/0210786 A1 9/2007 Allen et al.
2007/0270781 A1* 11/2007 Burgermeister .......... A61F 2/95 604/528
2008/0015421 A1 1/2008 Penner
2008/0071248 A1 3/2008 Delgado et al.
2008/0071339 A1 3/2008 Stalker et al.
2008/0176271 A1 7/2008 Silver et al.
2008/0183247 A1 7/2008 Harding
2008/0269573 A1 10/2008 Najafi et al.
2008/0269829 A1 10/2008 Li et al.
2008/0281212 A1 11/2008 Nunez et al.
2009/0115396 A1 5/2009 Allen et al.
2009/0209950 A1* 8/2009 Starksen ............ A61B 18/1492 606/41
2009/0221855 A1 9/2009 Walter et al.
2009/0224773 A1 9/2009 Joy et al.
2009/0224837 A1 9/2009 Joy et al.
2009/0275956 A1 11/2009 Burnes et al.
2010/0026318 A1 2/2010 Kroh et al.
2010/0030115 A1 2/2010 Fujimoto et al.
2010/0100055 A1 4/2010 Mustapha
2010/0161004 A1 6/2010 Najafi et al.
2010/0308974 A1 12/2010 Rowland et al.
2011/0009944 A1 1/2011 Moser
2011/0046452 A1 2/2011 Najafi et al.
2011/0063088 A1 3/2011 Stevenson et al.
2011/0092955 A1 4/2011 Purdy et al.
2011/0106120 A1* 5/2011 Haselby ............. A61M 1/3659 606/153
2011/0303229 A1* 12/2011 Najafi .................. A61M 25/01 128/899
2012/0286934 A1 11/2012 Rowland et al.
2013/0102858 A1 4/2013 Hill et al.
2015/0208929 A1 7/2015 Rowland et al.
2016/0324443 A1 11/2016 Rowland et al.
2020/0022601 A1 1/2020 Song et al.
2020/0297218 A1 9/2020 White et al.
2021/0068681 A1 3/2021 Campbell et al.
2021/0275733 A1 9/2021 Goldshtein et al.

FOREIGN PATENT DOCUMENTS

HK 1147906 8/2011
JP 2000-005136 1/2000
JP 2000-517073 12/2000
JP 2002-515278 5/2002
JP 2003-144417 5/2003
JP 2005-284511 10/2005
JP 2006-512112 4/2006
JP 2006-309582 11/2006
JP 2007-210547 8/2007
JP 2007-256287 10/2007
JP 2008-022935 2/2008
JP 2008-532590 8/2008
JP 2010-538254 12/2010
WO 2004/045407 6/2004
WO 2005/018507 3/2005
WO 2005/107583 11/2005
WO 2006/070278 7/2006
WO 2006/096582 9/2006
WO 2006/130488 12/2006
WO 2007/030489 3/2007
WO 2008/091409 7/2008
WO 2008/098255 8/2008
WO 2008/115456 9/2008
WO 2008/137703 11/2008
WO 2009/146089 12/2009
WO 2010/117356 10/2010
WO 2010/117597 10/2010
WO 2012/015955 2/2012
WO 2014170771 A1 10/2014
WO 2017115112 7/2017

OTHER PUBLICATIONS

Patent Cooperation Treaty (PCT), International Search Report and Written Opinion for application PCT/US2013/059769, mailed Dec. 13, 2013, International Searching Authority, US.

Patent Cooperation Treaty (PCT), International Search Report and Written Opinion for application PCT/US2011/045583, mailed Nov. 23, 2011, International Searching Authority, NL.

Extended European Search Report for application EP12804636.4, PCT/2012044998, dated Jan. 20, 2015, European Patent Office, Germany.

AU Patent Examination Report No. 1 for application AU2012275126, issue date Apr. 9, 2016, Australian Government IP Australia, Australia.

CN Notification of the First Office Action for application CN201280041807.9, issue date Mar. 23, 2015, State Intellectual Property Office of People's Republic of China, China.

CN Notification of Second Office Action for application CN201280041807.9, issue date Dec. 8, 2015, State Intellectual Property Office of People's Republic of China, China.

JP Office Action for application JP2014-519163, prepared May 25, 2016, mailed May 31, 2016, First Patent Examination Department, Japan.

Patent Cooperation Treaty (PCT), International Search Report and Written Opinion for application PCT/US2012/44998, mailed Sep. 25, 2012, International Searching Authority, US.

Patent Cooperation Treaty (PCT), International Search Report and Written Opinion for application PCT/US2011/045581, mailed Oct. 18, 2011, International Searching Authority, US.

Patent Cooperation Treaty (PCT), International Search Report and Written Opinion for application PCT/US2008/69229. mailed Oct. 1, 2008, International Searching Authority, US.

Abrams, Synopsis of Cardiac Physical Diagnosis, 1989, Lea & Febiger, pp. 25-29.

Ganong, Review of Medical Physiology, 2003, 21st edition, The McGraw-Hill, Inc., Chapter 29, pp. 569-573.

Allen et al., Moss and Adams' heart Disease in Infants, Children, and Adolescents, including the Fetus and Young Adult, 2001, Lippincott Williams & Wilkins, 6th edition, vol. 1, pp. 288-292.

AU Patent Examination Report No. 1 for application AU2010235020, issue date Aug. 18, 2014, Australian Government IP Australia, Australia.

CA Examination Report for application CA2757952, PCT/US2010/027951, dated Oct. 28, 2015, Canadian Intellectual Property Office, Canada.

Extended European Search Report for application EP10762085.8, PCT/2010027951, dated Jan. 4, 2013, European Patent Office, Germany.

JP Office Action for application JP2012-504690, prepared Jan. 10, 2014, mailed Jan. 21, 2014, 4th Patent Examination Department, Japan.

JP Office Action for application JP2012-504690, prepared Nov. 19, 2014, mailed Nov. 25, 2014, 4th Patent Examination Department, Japan.

(56) References Cited

OTHER PUBLICATIONS

JP Office Action for application JP2012-504690, prepared Oct. 30, 2015, mailed Nov. 4, 2015, 4th Patent Examination Department, Japan.
KR Notice of Office Action for application KR10-2011-7026250, dated Mar. 22, 2016, The Korean Intellectual Property Office, Korea.
TW Office Action Notice for application TW100109414, issued Jul. 24, 2014, Taiwan Intellectual Property Office, Taiwan.
PK Examination Report for application PK189/2011, emailed Jun. 6, 2013, Pakistan Patent Office, Pakistan.
Haynes, H.E. & Witchey, A.L., Medical Electronics; The Pill That "Talks" DEP, 1960, pp. 52-54, Cambden, New Jersey.
Collins, Carter, Miniature Passive Pressure Transensor for Implanting in the Eye, Transactions on Bio-Medical Engineering, vol. BME-14, No. 2, pp. 74-83, Apr. 1967.
Nagumo, J., Uchiyama, A., Kimoto, S., Watanuki, T., Hori, M., Suma, K., Ouchi, A., Kumano, M., and Watanabe, H., Echo Capsule for Medical Use (A Batteryless Endoradiosonde), IRE Transaction on Bio-Medical Electronics, pp. 195-199, 1962.
Patent Cooperation Treaty (PCT), International Search Report and Written Opinion for application PCT/US2010/27951. mailed Aug. 25, 2010, International Searching Authority, US.
Patent Cooperation Treaty (PCT), Written Opinion of the International Searching Authority for application PCT/US2008/03475, mailed Aug. 4, 2008, International Searching Authority, US.
Patent Cooperation Treaty (PCT), Written Opinion of the International Searching Authority for application PCT/US2009/39730, mailed Jun. 30, 2009, International Searching Authority, US.
International Preliminary Report on Patentability, Endotronix, Inc. PCT/US2012/034979, Nov. 7, 2013.
International Search Report and the Written Opinion of the International Searching Authority, Endotronix, Inc., PCT/US2012/34979, Nov. 2, 2012.
International Preliminary Report on Patentability, Nunez, Anthony, I. et al. PCT/US2008/003475, Sep. 24, 2009.
CN Notification of First Office Action for application CN201080020249.9, issue date Apr. 2, 2013, State Intellectual Property Office of People's Republic of China, China.
CN Notification of Second Office Action for application CN201080020249.9, issue date Feb. 21, 2014, State Intellectual Property Office of People's Republic of China, China.
CN Notification of Third Office Action for application CN201080020249.9, issue date Nov. 2, 2014, State Intellectual Property Office of People's Republic of China, China.
CN Notification of Decision or Rejection for application CN201080020249.9, date of mailing May 27, 2015, State Intellectual Property Office of People's Republic of China, China.
CN Notification of Fourth Office Action for application CN201080020249.9, issue date Mar. 30, 2016, State Intellectual Property Office of People's Republic of China, China.
Communication pursuant to Article 94(3) EPC from the European Patent Office; Application No. 10 762 085.8-1660; mailing date Jan. 26, 2015.
Communication pursuant to Article 94(3) EPC from the European Patent Office; Application No. 10 762 085.8-1660; mailing date Sep. 17, 2015.
Office Action from the USPTO; U.S. Appl. No. 13/860,851; Notification date Oct. 5, 2015.
Office Action in U.S. Appl. No. 16/727,230, mailed Apr. 25, 2024, 17 pages.
Office Action in U.S. Appl. No. 16/727,230, mailed Apr. 11, 2025, 14 pages.
Office Action in U.S. Appl. No. 16/727,230, mailed Oct. 24, 2025, 15 pages.

* cited by examiner 500
501
502
504
101
505
506
507
511
509
508
510
512

101
505
506
507
500
502

101
507
102
701
505
512
511
506

103
101
104
102
512
511
507

1102
102
1101
101
103
1401

1613
1616
1607
102
101
103
1614
1612
1615
1610
1600
1608

1713
1716
1707
101
102
103
1714
1712
1715
1710
1700

1813
1816
1817
1814
1812
1800

PRESSURE SENSOR, ANCHOR, DELIVERY SYSTEM AND METHOD

CROSS-REFERENCE TO RELATED APPLICATIONS

This application is continuation of U.S. application Ser. No. 14/428,551 entitled "PRESSURE SENSOR, ANCHOR, DELIVERY SYSTEM AND METHOD" and filed on Mar. 16, 2015 which claims priority to PCT Patent App. No. PCT/US2013/059769 entitled "PRESSURE SENSOR, ANCHOR, DELIVERY SYSTEM AND METHOD and filed on Sep. 13, 2013, U.S. Provisional Patent App. No. 61/701,058 entitled "PRESSURE SENSOR, ANCHOR, DELIVERY SYSTEM AND METHOD" and filed on Sep. 14, 2012.

FIELD OF INVENTION

This application relates to a medical implantable pressure sensor device, positioning and anchoring mechanism, delivery system and more particularly to a method for delivering and positioning the pressure sensor into the human body.

BACKGROUND

Delivery systems and positioning and anchoring devices are currently being used in medical procedures to guide and position devices from a remote site to a target site within a body. From a remote part of the body, a guidewire is introduced into an artery or vein. The guidewire is then advanced through the vascular system to the target site where the vascular implant is to be positioned. The guidewire then functions as a rail for the advancement of the delivery system.

Currently, delivery systems are used for accessing the anatomy and delivering many devices, both temporarily and permanently, into the body. Different devices and different anatomical target sites require different delivery system features and require different anchoring and positioning mechanisms. For example, a target vascular site is the right pulmonary artery and middle lobe vessel. There are often many turns and anatomical structures to navigate around and through to reach the desired site. If the delivery system or the positioning/anchoring mechanism for the delivery system lack certain critical features, the procedure may not be able to be performed. For example if the anatomy is quite tortuous and if the delivery system is not able to negotiate this tortuous anatomy the procedure may not be possible. As another example, there may not exist a specific delivery system designed and built for the specific implant and target anatomy; in these cases the physician is left to select generally available off-the-shelf accessories such as sheaths and wires to deliver the implant as best he or she can.

As can be appreciated from the above examples, multiple features are required to achieve desired parameters such as softness to reduce trauma to the vessel during insertion, minimal diameter to enable ingress through restricted passages in the vessels and facilitate access to the target site, stiffness/rigidity to allow pushability and resistance to kinking and to facilitate function of the delivery system once placed. Relative to the implant positioning and anchoring mechanism, it is critical to position the implant for optimal visualization, readability, and to reduce the risk of possible occlusion and/or or flow obstruction.

Therefore, it would be advantageous to provide a delivery system which facilitates delivery of a specific implant by providing optimal diameter, pushability, flexibility and stiffness without requiring additional accessory devices, thereby reducing or eliminating the risk of unsuccessful implant delivery. It would further be advantageous to provide adequate flow around the implant in the target location and the atraumatic positioning and anchoring mechanism needs to maintain the position of the implant, without risk of structural failure or partial disintegration, over the life of the patient.

SUMMARY

The present invention provides a medical device delivery system comprising an implant and assembly for placement over a guidewire.

In an embodiment the delivery system includes an implant, such as a wireless sensor, a first sheath, and a second sheath. The sheaths extend from a proximal end of the implant delivery system, and at least said first sheath extends to a distal end of said implant delivery system. The first sheath is positioned at least partially within said second sheath. The implant is connected to an exterior surface of the first sheath and positioned near an end of the second sheath. The first sheath and said second sheath are movable with respect to one another to deploy said implant to a desired location.

In an embodiment, the first sheath and said second sheath are rotatable about a common axis.

In an embodiment, a portion of said first sheath comprises a first geometry, and a portion of said second sheath includes a second geometry shaped to engage the first geometry to allow translation of said first sheath with respect to said second sheath and to prevent rotation of the first sheath with respect to said second sheath. The geometry may be any appropriate shape and size.

In an embodiment, the delivery system may comprising a wire extending from the second sheath and connecting to the first sheath, wherein the wire engages said implant. In an embodiment, the wire is not accessible directly from a proximal end of the first and second sheaths.

In an embodiment, the delivery system includes a third sheath. The first sheath and second sheath may be positioned at least partially within said third sheath. The second sheath may be able to translate with respect to said first sheath and said third sheath, and the first sheath and third sheath may be fixed relative to one another. In an embodiment, the first sheath and second sheath are capable of rotation and translation with respect to said third sheath.

In an embodiment, at least one of said first and second sheaths comprises a braided wire within the sheath wall.

In one example, an implant delivery system comprises an implant, an implant anchoring mechanism, a fixation loop, a positioning rod, and one or more sheaths attached at their proximal end to a handle assembly. The implant, with anchoring mechanism compressed for delivery, may be attached securely to the delivery system.

In an embodiment, the implant with anchoring mechanism may be secured wholly within or partially within a sheath during delivery. Manipulation of sheaths or other mechanisms may allow deployment of the implant anchors. Multiple anchors may be deployed at the same time or at different times. The positioning rod allows controlled positioning of the implant before, during, and after deployment of the implant anchors when controlled at the proximal handle assembly. The implant may be released from the delivery system by releasing the positioning rod from the implant fixation loop once the implant has been confirmed to be in the desired location with the anchoring mechanism fully deployed. The delivery system may then be retracted. In other embodiments, the implant may not have a fixation loop and the positioning rod may attach to and be released from the implant by other attachment means.

In an embodiment, the medical device delivery system is designed to implant a medical device fully intravascularly within a blood vessel. In an embodiment the implant may be a wireless sensor.

BRIEF DESCRIPTION OF THE DRAWINGS

Preferred embodiments of the present disclosure are described herein with reference to the drawings wherein.

DETAILED DESCRIPTION OF THE PREFERRED EMBODIMENTS

Reference will now be made in detail to embodiments of the invention, examples of which are illustrated in the accompanying drawings. It is to be understood that other embodiments may be utilized and structural and functional changes may be made without departing from the respective scope of the invention. As used herein, the term "proximal" refers to closer to the user and the term "distal" refers to further from the user.

Figure 1:
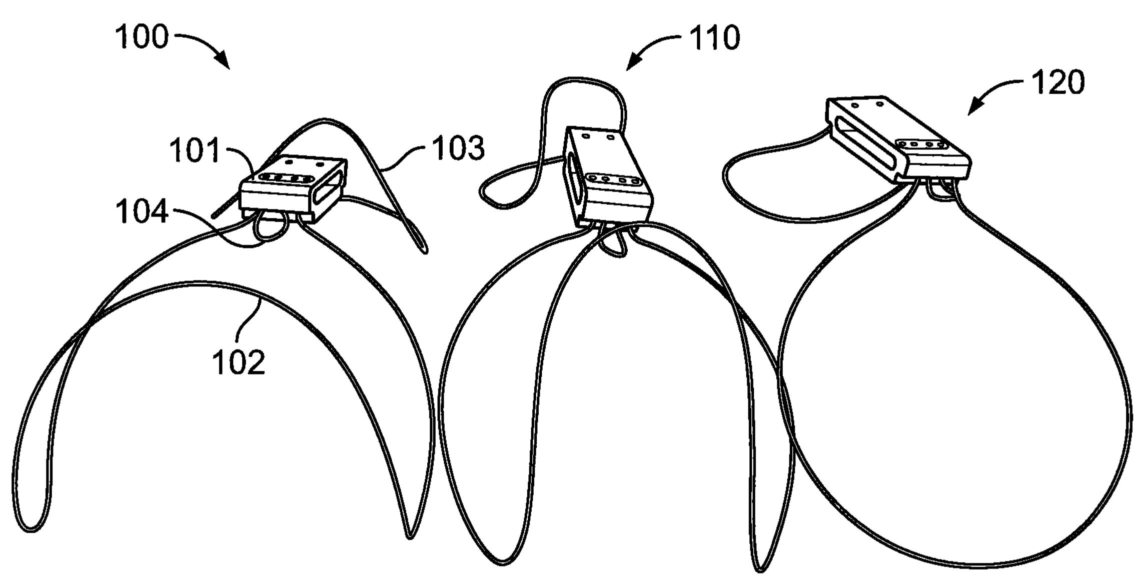
FIGS. 1 and 2 show designs of an implant, including an exemplary implant body and anchors.
Figure 2:
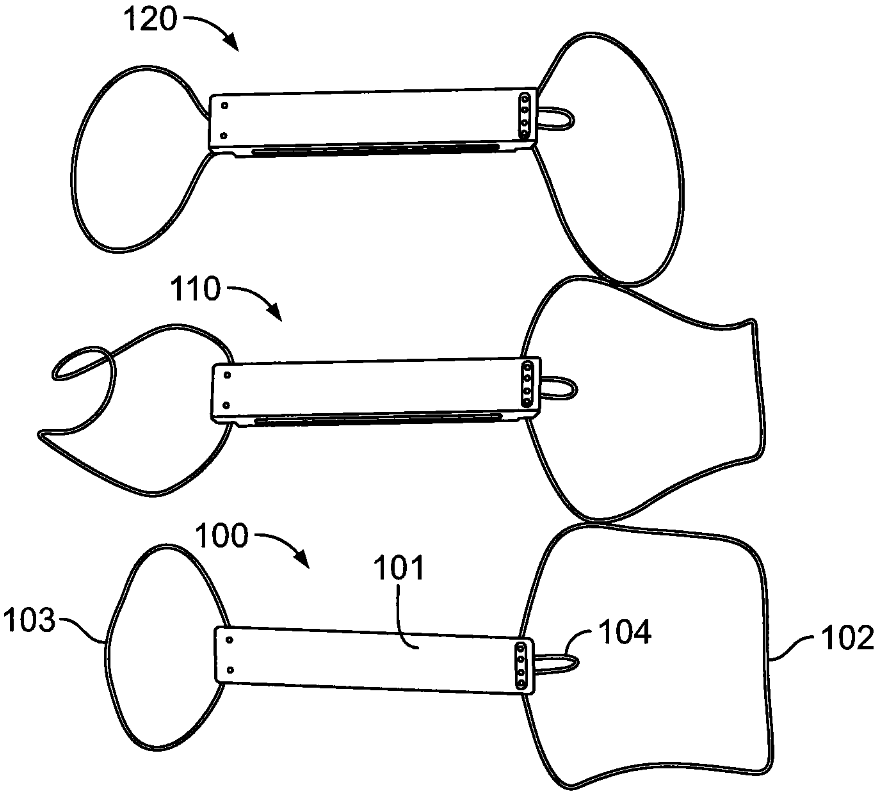

A medical device delivery system is generally presented. The medical device delivery system may comprise an implant delivery system having multiple components, movable with respect to one another to deliver and release an implant. The medical device delivery system of the present invention may be particularly useful for implanting a device within a blood vessel. In an embodiment the implanted device may be a wireless pressure sensor and the blood vessel is the pulmonary artery. FIGS. 1 and 2 show an exemplary implant design amenable to permanent implantation within a blood vessel. The implant 100 comprises an implant body 101, proximal anchor 102, distal anchor 103, and fixation element 104. The implant body, anchors, and fixation element may be of many different general sizes and shapes depending on the target implant location and intended function. In some embodiments, the implant 100 has no separate fixation element distinct from implant body 101, proximal anchor 102, or distal anchor 103. In other words, in some embodiments the implant body, proximal anchor, or distal anchor may be used individually or in combination to position and control the implant with respect to the delivery system.

The implant anchors 102 and 103 may attach to the implant body and may extend away from the implant body. The implant anchors 102 and 103 may be generally smoothly curved to gently conform to the walls of a blood vessel and actively secure the implant body 101 in a desired location. In an embodiment, the anchors 102 and 103 may secure the implant body 101 against the wall of a blood vessel. The anchors 102 and 103 may establish multiple points of contact along the vessel wall on the same or different planes relative to the implant body 101 to secure the implant body 101 in a desired location. The anchors 102 and 103 must be stiff enough to actively engage the vessel walls and maintain the location and orientation of the implant body 101, but flexible enough to not stress the vessel walls to the point of damage. In an embodiment, a suitable material for anchors 102 and 103 is a shape memory material such as Nitinol. Nitinol wire can be formed into a desired shape, with wire sizes typically ranging from 0.004" diameter to 0.010" diameter. Distal anchor 103 may be of the same or different general size, shape, and material of proximal anchor 102. In an embodiment, distal anchor 103 may be of smaller dimension than proximal anchor 102. Such a design may be beneficial for implantation along a narrowing section of a blood vessel, as the blood vessel may taper to smaller diameter distally to blood flow. Such a design may also be beneficial for placement of the distal anchor distal to a bifurcation while the implant body and proximal anchor reside proximal to the bifurcation. Implants 110 and 120 show alternative designs for implant anchors to secure an implant intravascularly. In an embodiment, an implant anchoring mechanism may be made from Nitinol or other similar materials and designed to be released into vessels of, but not limited to, between about 5 and 15 mm in diameter or between about 15 mm and 30 mm in diameter.

FIG. 2 shows implants 100, 110, and 120 in a view from above. The implant body 101 may be generally long and narrow so that the cross section is small in size to reduce obstruction of blood flow when positioned inside a blood vessel. The implant body 101 may generally be less than 33%, or in an embodiment may be less than 25%, or in another embodiment may be less than 15% of the cross sectional area of a vessel. In an embodiment, a fixation element 104 may be attached to the implant body 101 to facilitate delivery, positioning, and or removal of the implant. Fixation element 104 may be of various sizes and shapes. In an embodiment, fixation element 104 may be comprised of Nitinol wire forming a handle or loop extending from the implant body 101.

Figure 3:
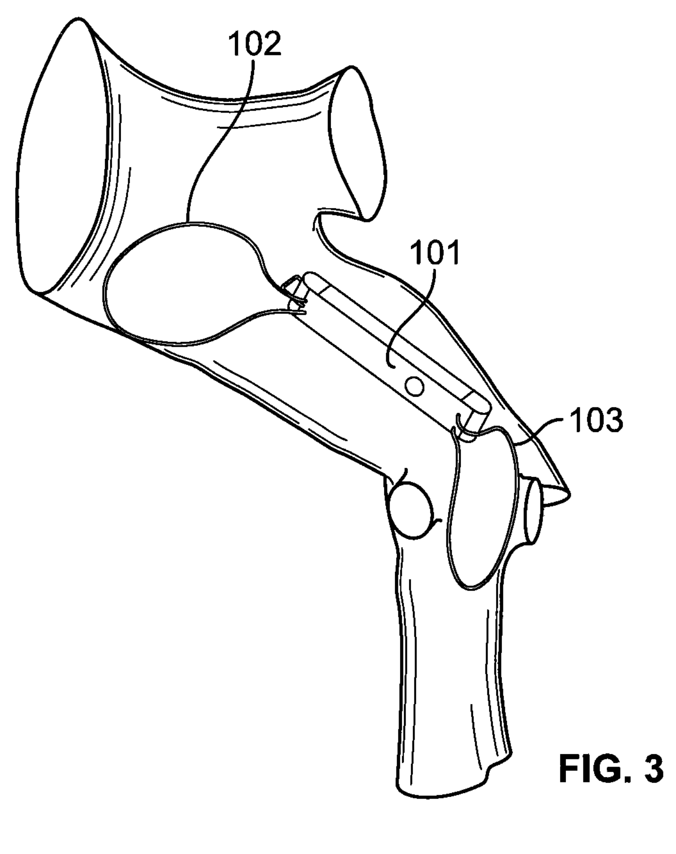
FIGS. 3 and 4 show an implant deployed in a location in the pulmonary artery.
Figure 4:
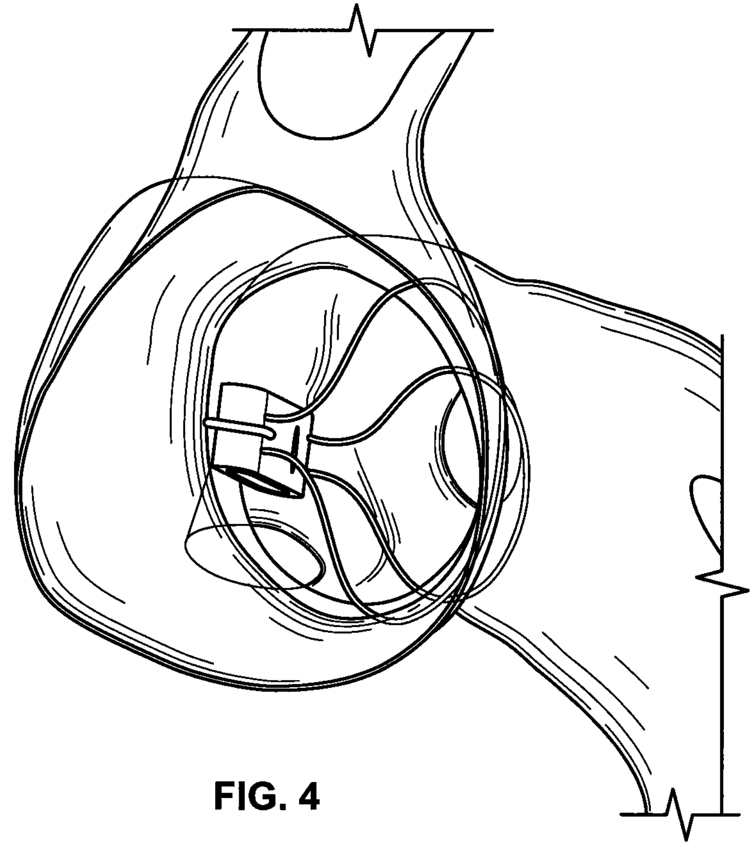

FIGS. 3 and 4 show implant 120 inside a section of the right pulmonary artery. The anchors 102 and 103 may contact the vessel walls on the same plane or a different plane contacted by the implant body 101. The anchors 102 and 103 may be designed to secure the implant within a generally straight vessel, a curved vessel, or a vessel with multiple branches such as at a bifurcation. It is desirable for one implant anchor design to be capable of securing an implant in several geometric configurations to account for variation in patient anatomy or for placement of the same implant design in different locations of the patient anatomy. For example, it may be beneficial in some patients to place the implant in the lower left lobe of the pulmonary artery, which often times is a generally straight, relatively long vessel that runs nearly parallel and in close proximity to the patient's spine. In other patients, it may be beneficial to place the same implant in an intermediate section of the right lobe of the pulmonary artery, for example, distal to the bifurcation of the main pulmonary artery trunk but proximal to the lower lobe of the right pulmonary artery. This section of the pulmonary artery often runs nearly parallel to a patient's rib and is in close proximity to the patient's chest with variable tapering and location and direction of bifurcations. FIGS. 3 and 4 show the distal anchor 103 engaging a proximal portion of the lower lobe of the right pulmonary artery at an angle to the implant body 101. The implant body 101 and the proximal anchor 102 engage a portion of the bronchus intermedius section of the pulmonary artery. The implant body 101 may be pressed against the wall of the vessel, stabilized in place by anchors 102 and 103 contacting the wall of the vessel in other locations.

Figures 21, 22, 23:
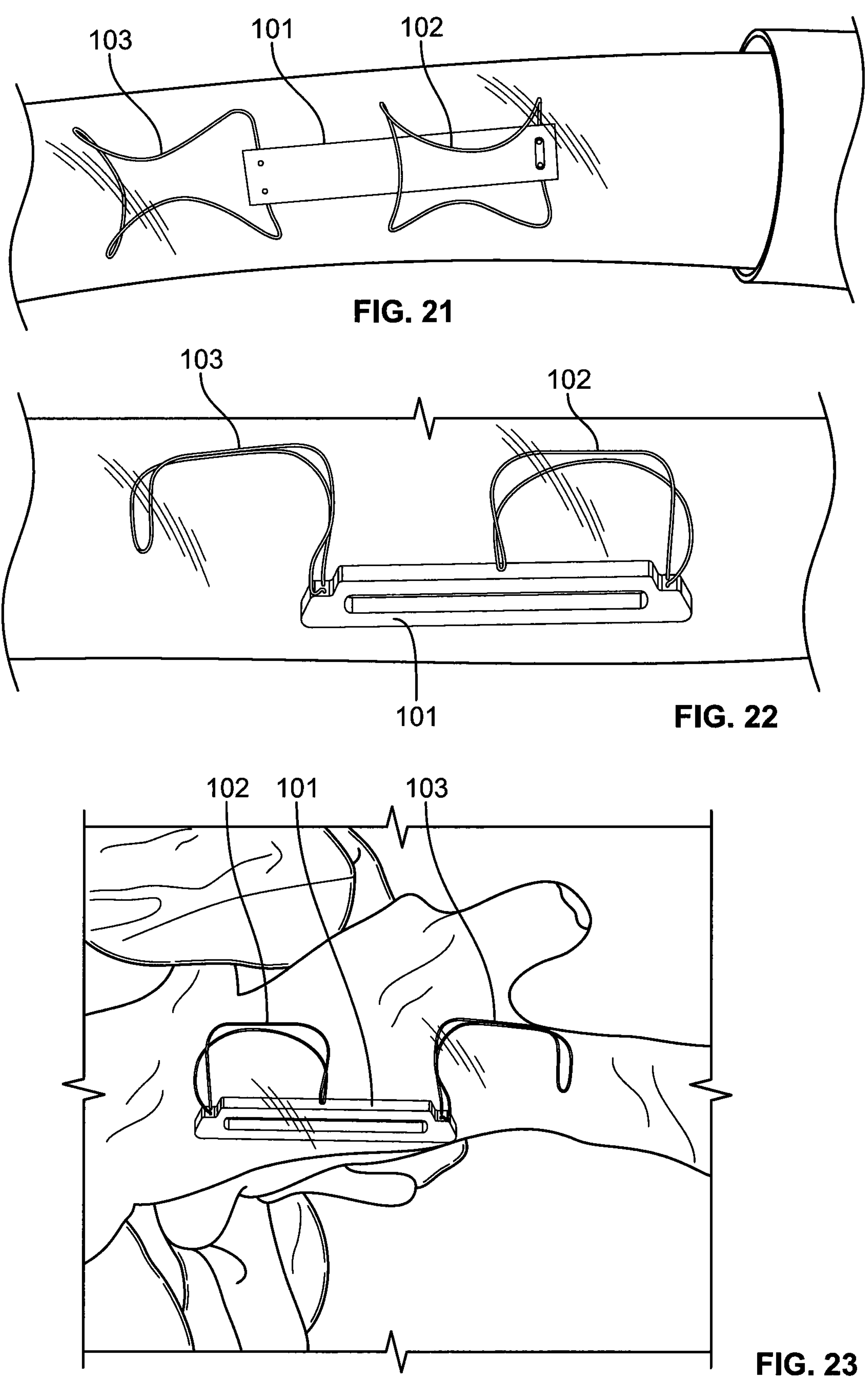
FIG. 21 shows a top view of one embodiment of the implant deployed in a straight vessel segment.
FIG. 22 shows a side view of the same embodiment of the implant deployed in a straight vessel segment.
FIG. 23 shows a view of the same embodiment of the implant deployed with a distal anchor distal a bifurcation and the implant body and proximal anchor proximal to the bifurcation.

In an embodiment, one or more anchors may secure the implant body 101 against one side of a vessel wall by applying pressure on the vessel wall opposite the side of the vessel wall contacting the implant body 101. In another embodiment, one or more anchors may provide pressure on the vessel wall along the length of the vessel wall. In yet another embodiment, anchors may contact the vessel wall opposite the implant body and semi circumferentially along different parts of the vessel wall. For example, one or more anchors may secure the implant body against one side of a vessel wall by extending from the implant body and forming contact points that: apply pressure along a length of the vessel wall, apply pressure on the vessel wall opposite the side of the vessel wall contacting the implant body, apply pressure again along a length of the vessel wall, and apply pressure on the same side of the vessel wall contacting the implant body. The anchors can be loops, saddle-shaped, dog-eared shaped, tongue-shaped, zig-zagged shaped, lasso shaped, or any other shape. In some embodiments, anchors with three-dimensional curvature and multiple planes of vessel wall contact are advantageous to provide stable orientation of the implant body against the vessel wall in both straight and angulated vasculature. FIGS. 21-23 show additional embodiments of implant anchors 102, 103 with three-dimensional curvature and multiple planes of vessel wall contact which are used to secure an implant body 101 against a vessel wall inside the central lumen of a vessel. FIGS. 21 and 22 show the anchors 102, 103 securing the implant body stable against a vessel wall for a straight section of a vessel with approximately constant cross section. FIG. 23 show the anchors 102, 103 securing the implant body 101 stable against a vessel wall where the distal anchor is placed distal to a bifurcation while the implant body and proximal anchor reside proximal to the bifurcation. The anchor curvature across the cross section of the vessel wall as well as along the length of the vessel assists the implant body 101 in maintaining a stable orientation against the vessel wall in straight, curved, angulated, and bifurcated sections of vasculature. The implant anchors 102, 103 are particularly effective for securing an implant in a target location where the target location has a vessel diameter that is less than the effective diameter of at least one of the implant anchors in an expanded position without compressive forces applied to the anchor. In such a target location, the expansion of the implant anchors will actively engage the vessel wall so that the vessel wall applies a compressive force to the anchor. In some embodiments, the compressive force of the vessel on at least one of the anchors is sufficient to secure the implant in the target location.

In another embodiment, a protrusion off the tip of the anchor may extend distally or proximally along a length of the vessel wall to provide additional contact area for stabilization and prevention of migration down or upstream. In an embodiment, a distal anchor may be sized to fit a 5 mm, 10 mm, or 15 mm diameter vessel. In another embodiment, a proximal anchor may be sized to fit a 10 mm, 15 mm, 20 mm, or 25 mm diameter vessel. In some embodiments, distal or proximal anchors may be comprised of Nitinol wire of diameter ranging from 0.004" to 0.010".

It is often desirable to deliver an implant through a delivery catheter with as small a diameter as possible to allow entry into small diameter vessels. In addition, smaller diameter delivery catheters require smaller incisions for implantation, which can reduce the risk of complications when closing the vascular access. The size of the delivery system is generally defined by the size of the implant device. To reduce the size of incision required for vascular access for a given implant size, it may be advantageous to deliver an implant without a sheath fully covering the implant body during delivery. A sheath over the implant body increases the amount of material and overall cross sectional area around the implant body. This increase in overall cross sectional area could require an increase in the diameter of an introducer sheath and ultimately an increase in the size of an incision required for vascular access.

Figures 5, 6:
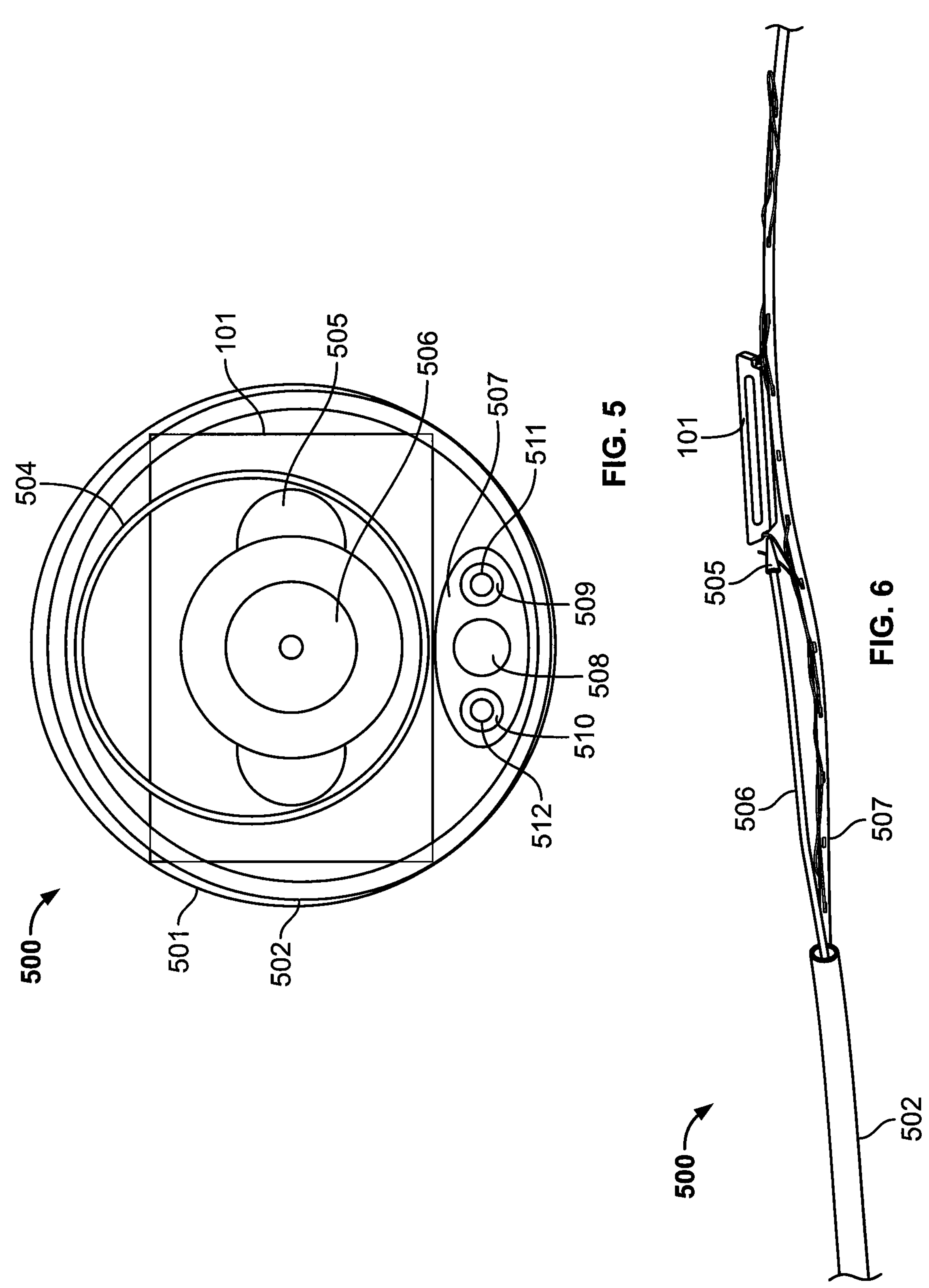
FIG. 5 illustrates a cross-sectional view of the delivery device from proximal the implant body looking distally into the page.
FIG. 6 shows a side view of the delivery device.
Figures 7, 8:
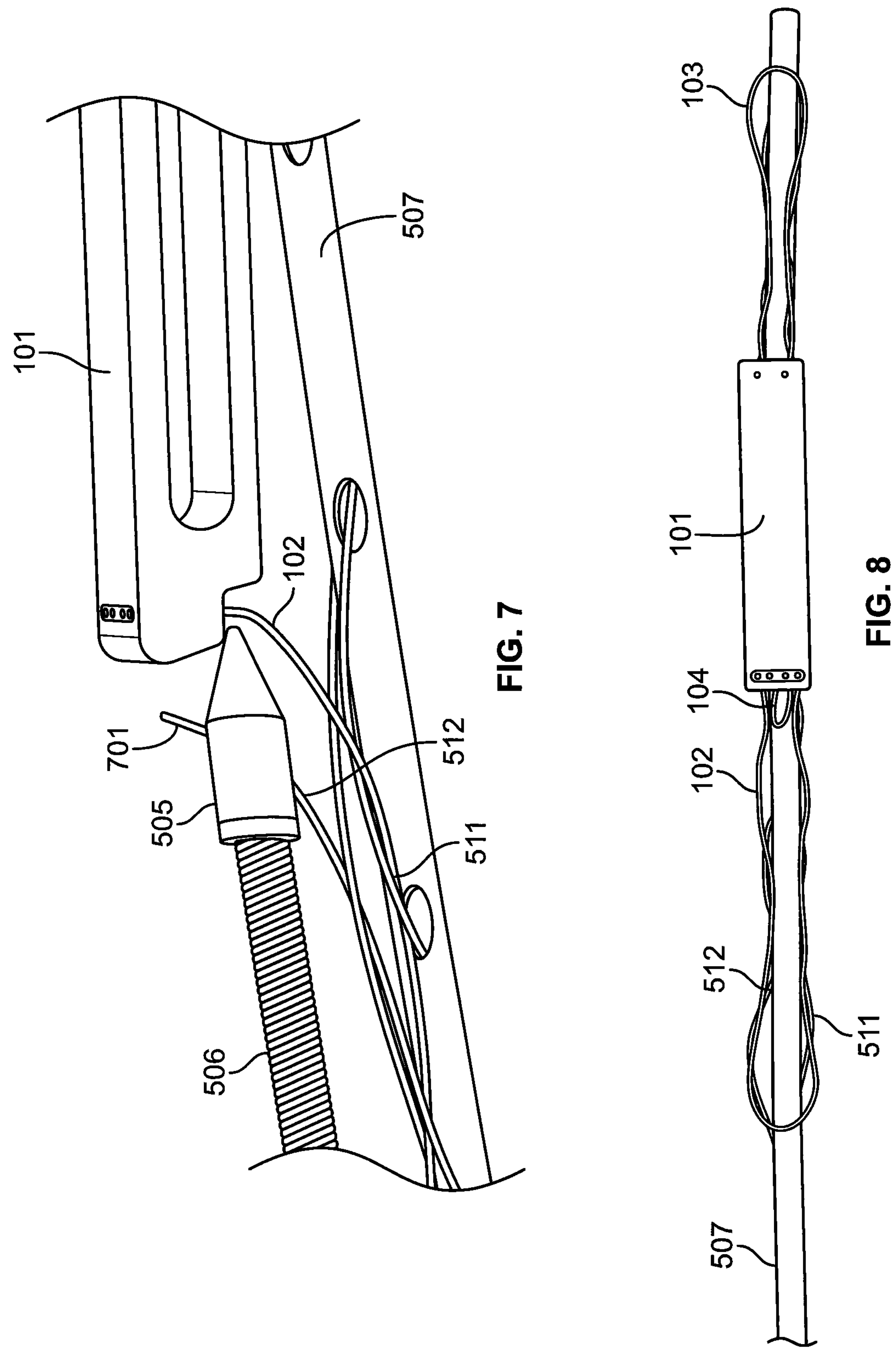
FIG. 7 shows a close up view of the delivery device attachment to the proximal end of the implant body.
FIG. 8 shows the implant secured to a carrier sheath.

FIG. 5 shows a cross section of a medical device delivery system 500 that maximizes the cross sectional area of an implant body 101 that may be delivered through an introducer sheath 501 of fixed size. FIGS. 6 and 7 depict side views of the same conceptual assembly. The cross section of FIG. 5 is a view from proximal the implant body 101 looking distally into the page. The entire medical device delivery system 500 fits within the introducer sheath 110, but the support sheath 502 does not extend distally (into the page) to cover the implant body 101. Proximal to implant body 101, support sheath 502 surrounds positioning sheath 504, positioning rod 506, and carrier sheath 507. Support sheath 502, positioning sheath 504, positioning rod 506, and carrier sheath 507 extend proximally (out of the page) to a handle assembly. In an embodiment, implant body 101 and carrier sheath 507 extend distally beyond the distal most end of support sheath 502. Support sheath 502, positioning sheath 504, and carrier sheath 507 may all be of sufficiently small size and/or of deformable configuration such that the minimum circular diameter introducer sheath that implant body 101 may physically fit into is governed entirely by the size of implant body 101.

The medical device delivery system 500 has several advantageous features for delivering an intravascular implant. The carrier sheath 507 may have multiple lumens extending the length of the sheath. Guidewire lumen 508 allows advancement of the delivery system to a target site in the anatomy over a guidewire, which may be inserted in guidewire lumen 508 to function as a rail for the advancement of the delivery system. Anchor attachment lumens 509 and 510 provide means to secure implant anchors in a collapsed position to the medical device delivery system 500 during delivery. Ties 511 and 512 or wires may be used to assist in collapsing one or more anchors to a compact configuration for delivery. Disengaging, retracting, or breaking ties or wires may deploy the implant from the carrier sheath 507. Positioning rod 506 may attach to fixation attachment head 505, which enables the positioning rod to clasp implant body 101. Positioning rod 506 should be flexible enough to easily traverse the delivery path of tortuous anatomy, stiff enough to enable pushability, and rigid enough to allow for approximately 1:1 torqueability. In an embodiment, one or more of the implant anchors may be deployed from the carrier sheath 507 prior to release of the implant from the positioning rod 506. The positioning rod thus allows for precise control of positioning and orientation of the implant prior to final release of the implant into its desired location. Positioning sheath 504 may shroud the positioning rod 506 from the handle to the proximal end of the implant body 101 to assist retraction of the positioning rod 506 and attachment mechanism from the implant body upon deployment. In one embodiment, one or more of positioning sheath 504 and positioning rod 506 may comprise a braided wire reinforced sheath, such as are found in guiding catheters. For example, a sheath, such as the positioning sheath 504, may include a braided wire within the sheath wall. In one embodiment, positioning rod 506 may be a multifilar cable. By selecting proper durometer materials and braiding, the positioning rod 506 and sheath 504 may provide proper pushability, flexibility, and torqueability to control the implant during delivery. In one embodiment, the positioning sheath 504 or support sheath 502 serves as a guide for the positioning rod 506, so that while friction applied to the walls of the positioning sheath 504 or support sheath 502 may limit the torqueability and control of the positioning sheath 504 or support sheath 502, the positioning rod 506 may be free of said friction and able to move freely within the lumen of positioning sheath 504 or support sheath 502.

FIG. 6 shows a side view of the medical device delivery system 500. In this view, carrier sheath 507 extends from within the support sheath 502, to underneath the implant body 101, all the way distally from the implant body 101. Support sheath 502 is shown in a retracted position. The distal end of support sheath 502 may be positioned adjacent the proximal end of implant body 101. In one embodiment, support sheath 502 may allow torqueability of the delivery system. Positioning sheath 504 is contained inside support sheath 502, and is not visible in this view. Positioning rod 506 extends from within support sheath 502 to the proximal end of implant body 101. A fixation attachment head 505 attaches to the distal end of positioning rod 506 to allow the positioning rod assembly to be controllably secured to the implant body 101.

FIG. 7 shows a close up view of the distal end of the positioning rod 506 and fixation attachment head 505 controllably securing the proximal end of the implant body 101. In an embodiment the fixation attachment head 505 is secured to the implant body 101 by inserting a fixation element on the implant body 101 into the fixation attachment head 505. A fixation wire 701 may be inserted into the fixation attachment head 505, in order to engage a portion of a fixation element 104 on the implant body 101 to controllably secure the implant body 101 to positioning rod 506. The positioning rod 506 may be released from implant body 101 by retracting fixation wire 701. In an embodiment, fixation wire 701 may be retracted within support sheath 504. In an embodiment, this attachment enables precise control of the implant body during delivery, before and after anchor deployment, to position the implant body in a desired orientation and position. The positioning rod 506 and attachment head 505 may be attached to a fixation loop by various means, such as a suture loop, wire, wire with a coiled distal tip, hook, barb, interference fit, or various other methods known in the art.

FIG. 7 also shows an embodiment for securing a proximal implant anchor 102 to carrier sheath 507. In this embodiment, the anchor 102 extends outward from the implant body 101 towards the carrier sheath 507. Upon deployment, the spring forces of the anchor 102 may cause implant body 101 to move opposite the carrier sheath 507, facilitating retraction of carrier sheath 507. In an embodiment, ties 511 and 512 or wires may engage a portion of anchor 102 to assist in collapsing anchor to a compact configuration for delivery.

Figures 9, 10:
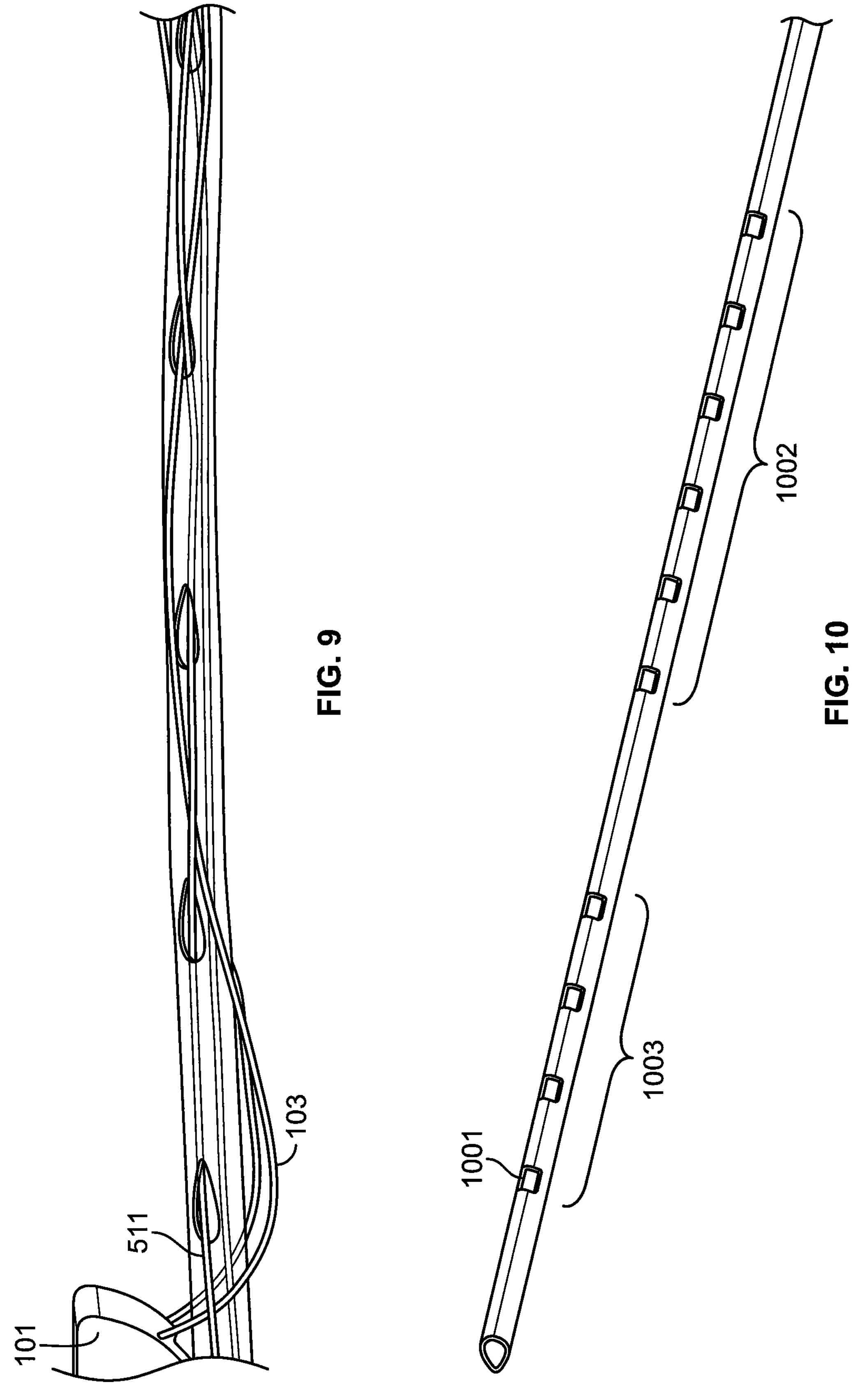
FIG. 9 shows a close up of the distal anchor secured to a carrier sheath.
FIG. 10 illustrates a section of a carrier sheath.

FIG. 8 shows the proximal anchor 102 and distal anchor 103 secured to the carrier sheath 507. FIG. 9 shows another view of the distal anchor 103 secured to the carrier sheath 507. In an embodiment, the implant body 101 is not directly secured to the carrier sheath 507 but is indirectly secured to the carrier sheath 507 via implant anchors 102 and 103 and optionally fixation element 104. FIG. 10 shows carrier sheath 507, with slots 1001 in carrier sheath. One or more slots in distal section 1003 may be used to secure a distal anchor 103 of implant and one or more slots in a proximal section 1002 may be used to secure a proximal anchor 102. In an embodiment, ties 511 and 512 or wires may be inserted at least partially in anchor attachment lumens 509 and 510. Ties 511 and 512 may exit carrier sheath 507 in a slot one location, engage a portion of an anchor, and re-enter the same slot or a different slot to assist in collapsing anchor to a compact configuration for delivery. One tie may be used for one or more anchors. In an embodiment, distal anchor 103 and proximal anchor 102 are secured by two tie wires 511 and 512. In an embodiment, tie wire 511 extends along one side of the carrier sheath 507 and tie wire 512 extends along another side of the carrier sheath 507. In an embodiment, tie wires 511 and 512 extend parallel to each other, and enter in and out of slots in carrier sheath. In an embodiment, tie wire 511 secures both the proximal anchor 102 and distal anchor 103 on one side of the carrier sheath 507, while tie wire 512 secures both the proximal anchor 102 and distal anchor 103 on the opposite side or carrier sheath 507, i.e. one tie wire secures one side of each anchor. In an embodiment, to deploy the implant anchors, tie wire 511 and 512 may be partially retracted to deploy the distal anchor 103 while the proximal anchor 102 remains tied to carrier sheath. In an embodiment, tie wire 511 and 512 may be retracted at the same time, so that both sides of the anchor deploy at the same time. In an embodiment, each tie wire has its own set of slots in carrier sheath such that the tie wires never cross. In another embodiment, anchors may be inserted into slots in carrier sheath 507. In yet another embodiment, the proximal anchor may not be attached to one of anchor attachment lumens 509 and 510 but may instead be constrained in a collapsed configuration by support sheath 502.

Figures 11, 12:
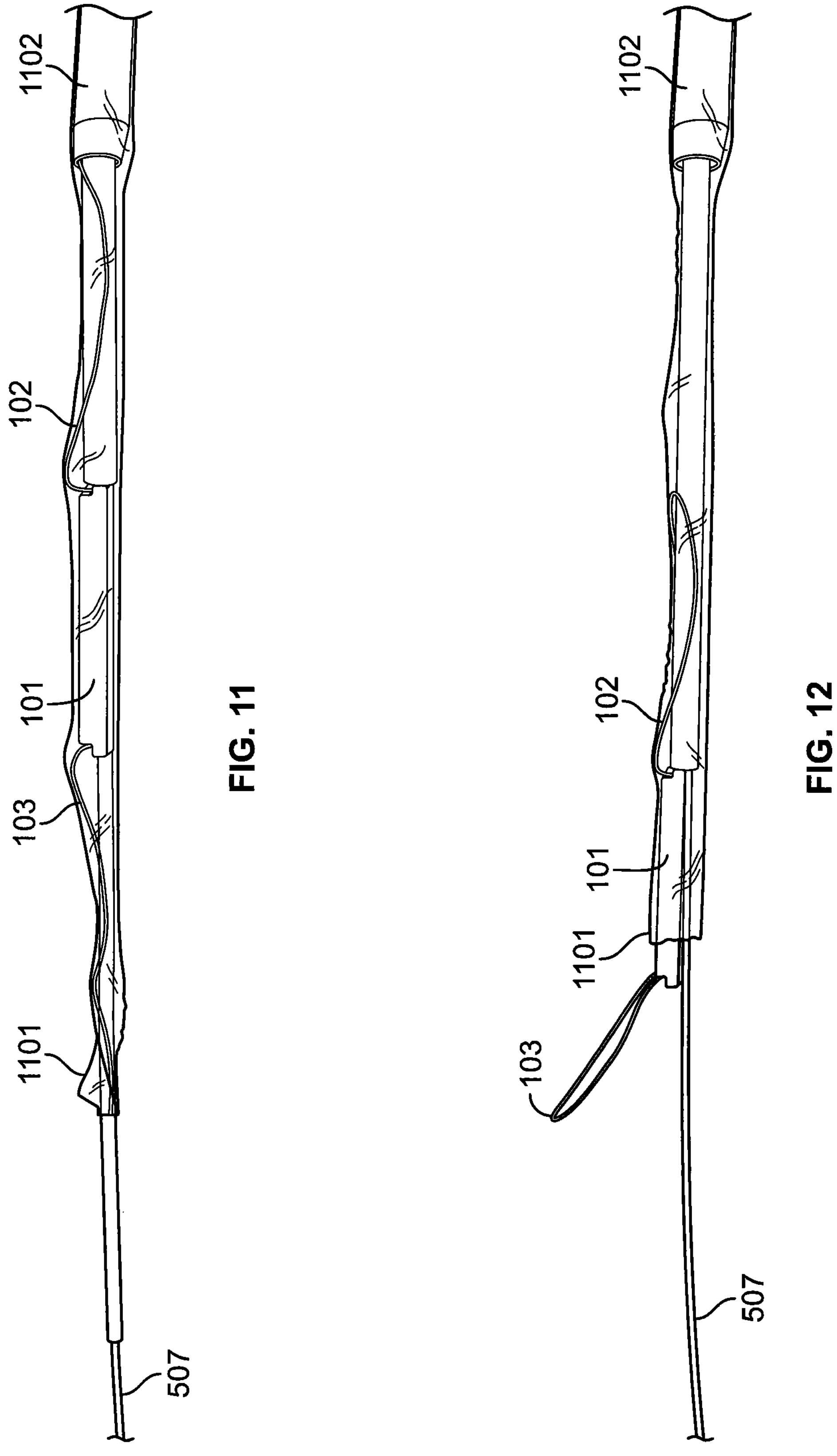
FIG. 11 shows another embodiment of the delivery system with the implant and anchors in a collapsed configuration.
FIG. 12 shows another embodiment of the delivery system with the implant and proximal anchor in a collapsed configuration and the distal anchor in an expanded configuration.
Figure 13:
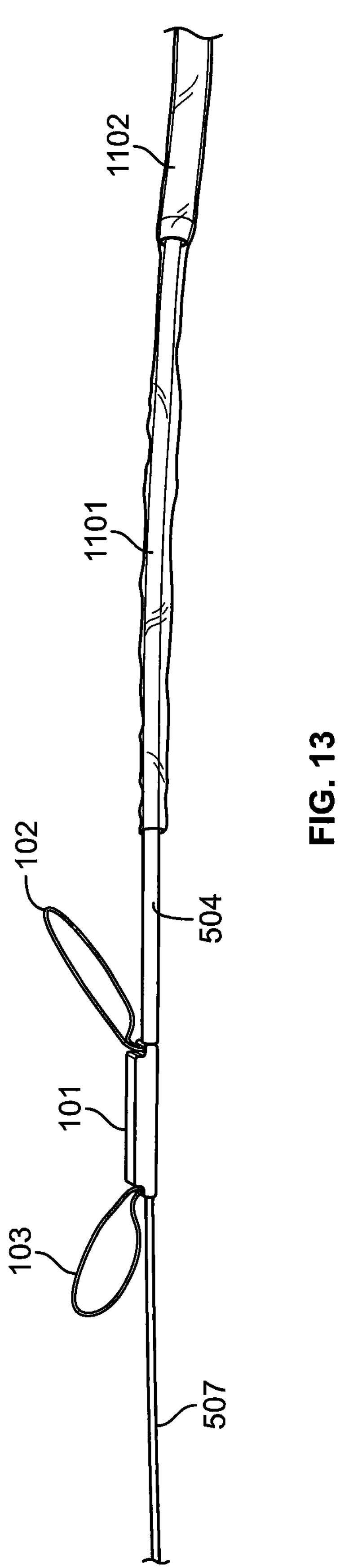
FIG. 13 shows another embodiment of the delivery system with the implant fully deployed.

In other embodiments, it may be desirable to have a sheath fully cover some or all of the implant body and distal implant anchor during delivery. FIGS. 11, 12, and 13 show another embodiment of the present invention. Support sheath 502 has a thin walled distal section 1101 and thick walled proximal section 1102. The thick walled proximal section 1102 provides sufficient stiffness to prevent kinking and provide torqueability. The thin walled distal section 1101 minimizes the cross sectional area of material covering the implant body while optionally providing sufficient stiffness to assist maintaining anchors 102 and 103 in a collapsed configuration during delivery. FIG. 12 shows the support sheath 502 in a partially withdrawn position, where the distal most end of the thin walled distal section 1101 no longer constrains distal anchor 103. FIG. 13 shows the support sheath 502 withdrawn further, where the distal most end of the thin walled distal section 1101 no longer constrains proximal anchor 102.

Figure 14:
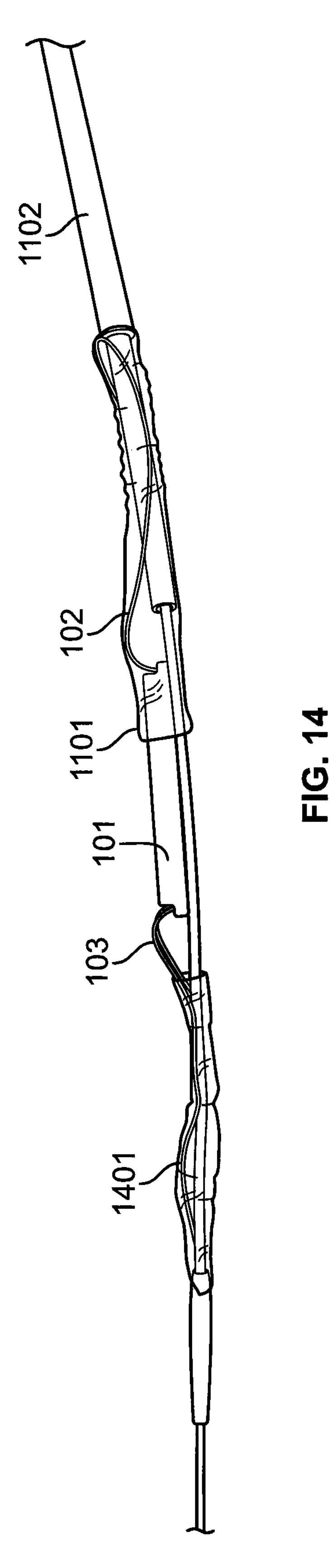
FIG. 14 shows another embodiment of the delivery system with the implant and anchors in a collapsed configuration.
Figures 15, 16:
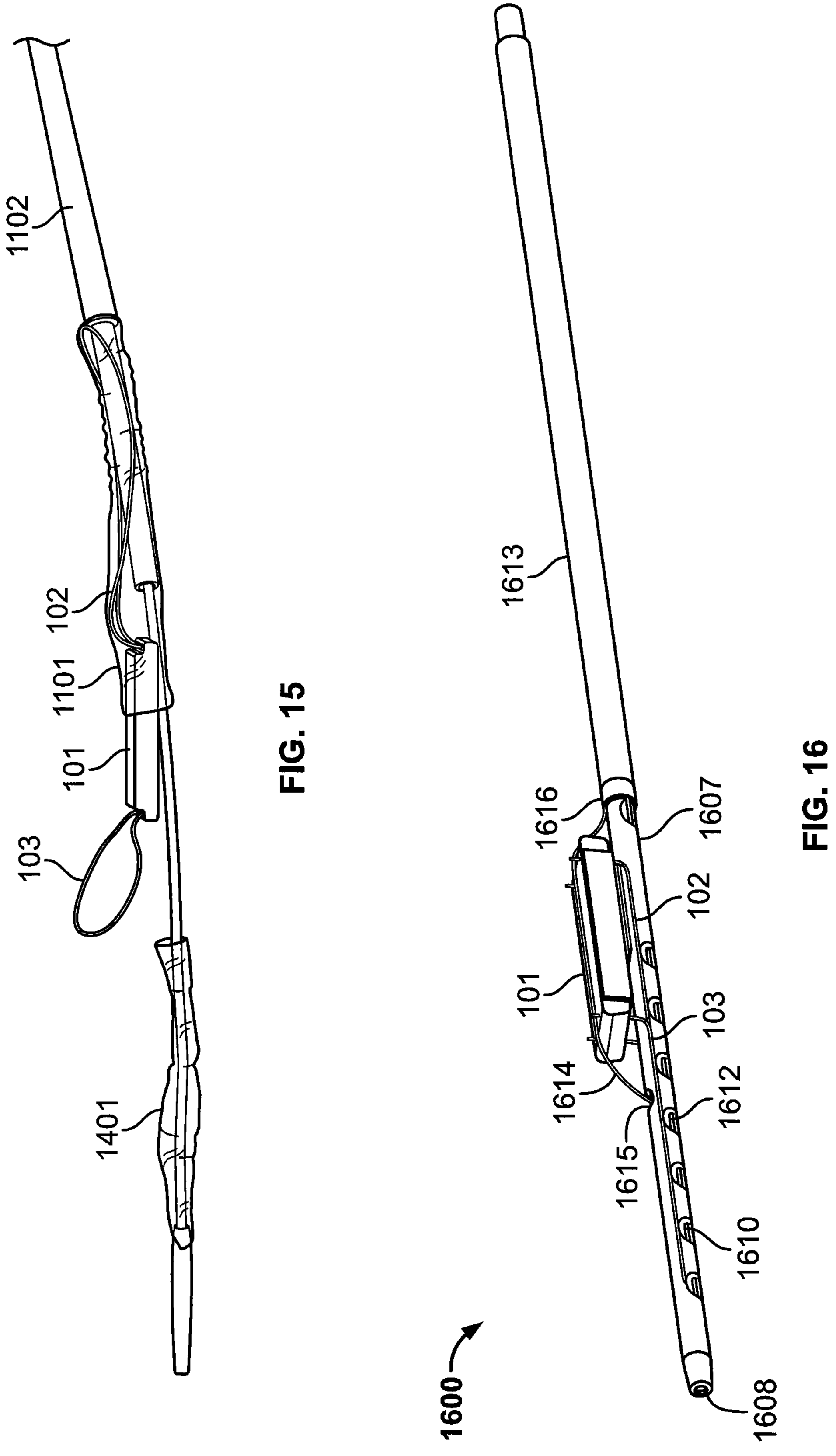
FIG. 15 shows another embodiment of the delivery system with the implant and proximal anchor in a collapsed configuration and the distal anchor in an expanded configuration.
FIG. 16 shows another embodiment of the delivery system in a perspective view.

FIGS. 14 and 15 show another embodiment of the present invention where the thin walled distal section 1101 of support sheath 502 may not cover the implant body 101 during delivery but a distal anchor support sheath 1401 maintains distal anchor 103 in a collapsed configuration during delivery. Such an embodiment may minimize the cross sectional area of material covering the implant body while distal anchor support sheath 1401 may also allow for a smooth transition from the tip of the medical delivery device to the implant body.

In an embodiment, the delivery system is advanced over a guidewire into the femoral vein, up the vena cava, into the right atrium, into the right ventricle, up into the pulmonary artery, and then, in an embodiment, into the right pulmonary artery. The delivery system, if desired, may then be advanced on into the bronchus intermedius of the pulmonary artery. In other embodiments, the delivery system may be advanced into another location in the pulmonary artery, such as the lower lobe of the left or right pulmonary artery. The delivery system may be advanced distally or retracted proximally, or may be rotated about an axis to achieve the desired location and orientation of the implant in the target site. The location and orientation may be checked via fluoroscopic imaging, or wirelessly via RF interrogation, ultrasound or other means.

In an embodiment, an implantation procedure may comprise the steps of:

1. Preparing delivery system (flush lumens, lubricate guidewire & delivery catheter).
2. Gaining femoral venous access with appropriate introducer.
3. Inserting Swan-Ganz type catheter into introducer and advance balloon distal end through the vasculature across the valves and into the target anatomy within the pulmonary arterial system.
4. Measuring pulmonary artery pressure using the Swan-Ganz by conventional means well known in the art.
5. Inserting a guidewire into the Swan-Ganz and advance the guidewire through the catheter until the distal end of the wire exits the distal end of the Swan-Ganz catheter. Removing the Swan-Ganz from the patient.
6. Inserting delivery catheter, with implant attached, over the guide wire and advance through the vasculature to the target anatomy.
7. Optionally, conducting a calibration and orientation check of the implant in-situ. Rotating implant by rotating catheter to achieve desired orientation, using fluoroscopy or other means as a guide.
8. When desired implant position and orientation are achieved, retracting anchor release ties to release distal anchor. In some embodiments of the invention, the distal anchor may be re-sheathed at this point, if desired, by advancing a support sheath back over it. This may facilitate last-minute corrections to positioning and orienting the implant.
9. Retracting support sheath (proximal to proximal anchor).
10. Retracting anchor tie to release proximal anchor.
11. Retracting carrier sheath until distal end is proximal to proximal anchor.
12. If desired, rotating implant again using positioning rod. Check that desired orientation is maintained.
13. Releasing implant from the delivery catheter (from the positioning rod) by first retracting fixation wire (short retraction length) and then retracting the positioning rod while the positioning sheath maintains the implant position.
14. Removing guidewire, introducer, and close vascular access.

In some instances, such as cases of pulmonary or tricuspid regurgitation or other anatomical difficulties, it may be advantageous to use a deflectable tip sheath instead of a Swan Ganz catheter to gain access to the desired pulmonary artery vasculature. A guide wire could be inserted through the deflectable tip sheath, allowing access for the implant delivery system over the guide wire. In another embodiment, the implant delivery system may be at least partially comprised of a deflectable tip sheath, such that the implant delivery system can be used to assist placement of the guide wire without the need for a catheter exchange.

In delivering a pulmonary artery implant, it may be advantageous to provide for certain features of the delivery system that aid the implanting physician. For example, the ability to inject contrast to image the implant in relation to vessel immediately prior to implant deployment could improve the safety and performance of an implant. Similarly, the ability to inject contrast to visualize the implant immediately post deployment without exchanging catheters can provide further confidence and confirmation of proper implant location. The lack of exchange can reduce the operating time and reduce the risk to the patient by limiting the number of sheaths traversing the tricuspid and pulmonary valves and chordae. Further, it could also be beneficial to immediately obtain a reference pulmonary artery pressure measurement after implant deployment, again without another catheter exchange that would lengthen the time and increase the risk of the procedure.

FIGS. 16-23 show one embodiment of a delivery system that provides such beneficial features. FIG. 16 shows a perspective view of a portion of such a delivery system. The handle assembly on the proximal end is not shown. Also not shown is a support sheath, which in an embodiment may extend from the distal end of the handle assembly up to near the proximal end of the implant. The support sheath may serve as a guide for the inner sheaths, so that while friction applied to the walls of the support sheath may limit the torqueability and control of the support sheath, the inner sheaths may be free of said friction and able to move freely within the lumen of support sheath. In one embodiment, the support sheath may be a braided sheath with stainless steel or other suitable materials or may be of a simple plastic such as HDPE, FEP, or other material with wall thickness sufficient to prevent kinking yet remain soft and flexible.

In one embodiment, two sheaths may run inside the support sheath. A torque sheath 1613 may extend from a handle on the proximal end to a location near the proximal end of the implant. A weld ring 1616 may be bonded to the proximal tip of torque sheath 1613. The weld ring may have multiple wires or other components bonded to it. In one embodiment, one or more anchor release wires 1612 and a protection wire 1614 may be bonded to the weld ring 1616. In one embodiment, the wires 1612 and 1614 are bonded to an outer surface of the weld ring 1616, and a portion of the torque sheath 1613 may extend over the wires 1612 and 1614 and weld ring 1616 to form a robust bond connecting the components. Protection wire 1614 may be a wire, ribbon, sheet or other suitable form and could be made of any suitable material such as Nitinol, stainless steel, plastic, or a Teflon coated stainless steel. Protection wire 1614 may be pre-shaped to conform to implant body 101. Pre-shaping protection wire 1614 may lower the profile of the implant assembly during delivery and may increase the columnar stiffness of the protection wire 1614 such that when advancing the implant assembly distally, friction forces generated on the protection wire 1614 are not of sufficient strength to push protection wire 1614 proximally and off the implant body 101. The protection wire 1614 may enter into and out of slots 1615 in carrier sheath 1607 to secure the wire in place during delivery. Slots 1615 may be distal and/or proximal to the implant body to aid fixation.

The carrier sheath 1607 may extend from a handle on the proximal end to a location distal the distal end of the implant 101 and implant distal anchor 103. The carrier sheath may have a central lumen 1608 to facilitate passage of a guide wire and allow the delivery of the implant delivery system from an access site to a target location in the body. Slots 1610 in the carrier sheath 1607 allow for anchor release wires 1612 to enter in and out of the carrier sheath 1607, engaging proximal anchor 102 and distal anchor 103 to hold anchors 102 and 103 in a collapsed position during delivery. Slots 1610 may be distal and/or proximal to the implant body to secure anchors 102 and 103 that may extend distally and/or proximally to the implant body.

Carrier sheath 1607 and/or torque sheath 1613 may be braided to allow torqueability. Carrier sheath 1607 and/or torque sheath 1613 may be attached at a proximal end, such as at a handle end to allow rotation and translation fixed relative to one another. In another embodiment, carrier sheath 1607 and torque sheath 1613 may also be attached at a distal end to allow rotation and translation fixed relative to one another. In one embodiment, carrier sheath 1607 and torque sheath 1613 may be temporarily fixed to each other such that fixed rotation and translation occurs when desired, but when not desired, carrier sheath 1607 and torque sheath 1613 may move relative to one another. In one embodiment, protection wire 1614 and anchor release wires 1612 may extend from a distal end of torque sheath 1613 and at least temporarily attach to carrier sheath 1607. In one embodiment, protection wire 1614 and anchor release wires 1612 attach to carrier sheath 1607 by entering into and out of slots 1615 and 1610 on carrier sheath. In one embodiment, additional features may allow the distal tip of the torque sheath 1613 to engage carrier sheath 1607, such as in a key-keyhole configuration, to allow the carrier sheath 1607 to move proximal/distal relative to the torque sheath but which prevents rotation of the carrier sheath 1607 relative to the torque sheath 1613. In one embodiment, carrier sheath 1607 and torque sheath 1613 are at least temporarily fixed at a proximal end and are also at least temporarily fixed at a distal end to facilitate rotation and translation of the carrier sheath 1607 and torque sheath 1613 together. The temporary fixation may be disengaged, such that torque sheath 1613 and carrier sheath 1607 may move relative to one another. In one embodiment, the distal tip of the torque sheath 1613 and carrier sheath 1607 may translate relative to one another but may not rotate relative to one another. In one embodiment, motion of the torque sheath 1613 relative to the carrier sheath 1607 may serve to disengage implant from carrier sheath 1607 and/or torque sheath 1613.

In an exemplary embodiment, an implant may be delivered to a target site with the embodiments described. The catheter delivery system 1600 of FIG. 16 is advanced from an insertion site, over a guide wire, to a target location in the anatomy. Features of the torque sheath 1613, carrier sheath 1607, and/or support sheath 1602 (not shown) enable the implant body 101 to be rotated at the target site. In one embodiment, contrast may be injected in the support sheath 1602 lumen in between the outer wall of the torque sheath 1613 and the inner wall of the support sheath 1602. Such an injection may allow visualization of the implant body 101 at the target site immediately prior to deployment. In an embodiment, the activation of a positive commit feature on a proximal handle end of the delivery system may enable the torque sheath 1613 to move relative to carrier sheath 1607. Activating a handle feature may enable the torque sheath 1613 to translate proximally while maintaining position of carrier the sheath 1607 and support sheath 1602. In an embodiment, the protection wire 1614 may be shorter than the anchor release wires 1612, such that the protection wire 1614 no longer covers the proximal end of implant body 101 prior to the anchor release wires 1602 disengaging the proximal anchor 102 and distal anchor 103. After deployment of the implant, a positive commit feature on a proximal handle end may enable the carrier sheath 1603 and torque sheath 1613 to be moved proximal to the deployed implant while the support sheath 1602 may be held in a fixed position. The implant delivery system is designed so that the carrier sheath 1602, torque sheath 1613, and/or guide wire may be moved proximal to the implant body 101 without causing the deployed implant body 101 or proximal anchor 102 and distal anchor 103 to move. In an embodiment, the carrier sheath 1607 and torque sheath 1613 may be removed from the support sheath 1602. In another embodiment, the guide wire may be maintained in position while the carrier sheath 1607 and torque sheath 1613 are removed from the body. Following implant deployment, contrast may be injected to confirm proper orientation and location of the implant. In the event the implant may be positioned sub-optimally, snares or other catheter tools standard in the industry may be inserted through the support sheath 1602 to aid in capturing or repositioning of the implant. The support sheath 1602 may also be used as a fluid column to obtain a reference pressure measurement. The support sheath 1602 may then be removed, leaving the implant in its deployed position in the body. In another embodiment, the torque sheath 1613 or carrier sheath 1607 may be rotated with respect to one another, such that the relative rotation causes the implant to be released from the sheaths. Other deployment means may also be possible, such as dissolving anchor release wires, cutting sutures, using laser or ultrasound energy to disengage the implant from the sheaths, or other means known in the art.

Figures 17, 18:
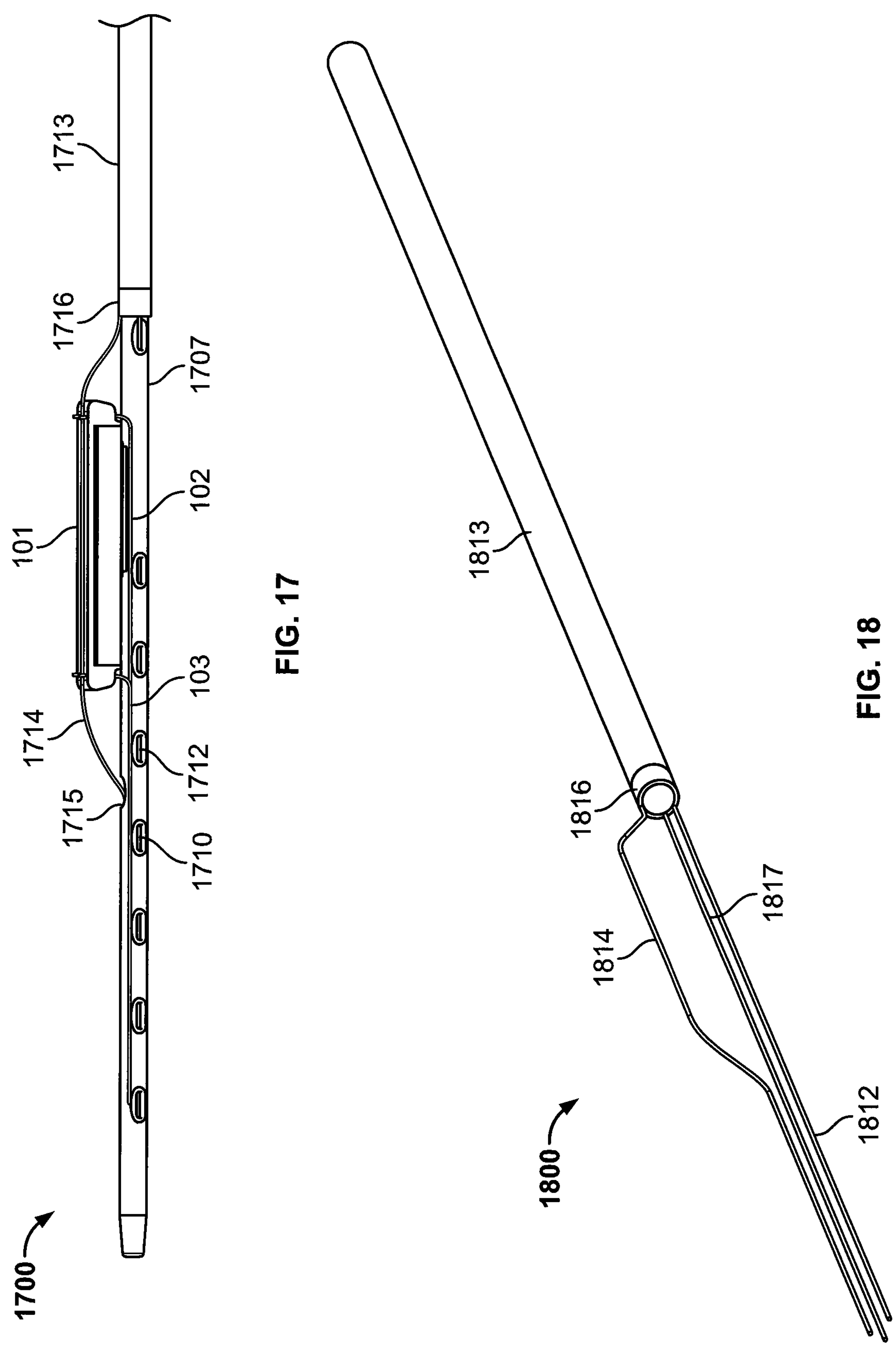
FIG. 17 shows the same embodiment in a side view.
FIG. 18 shows an embodiment where the anchor release wires and an implant protection wire are connected at a proximal end to the distal end of a sheath.

FIG. 17 shows a side view of a distal portion of said delivery system. Again in this image the support sheath 1702 is not shown. In one embodiment, in a delivery position, the proximal end of support sheath 1702 may extend from a distal end of a handle mechanism to a distal end of support sheath 1702 that is positioned distal the weld ring 1716 yet just proximal the implant body 101. In one embodiment, the protection wire 1714 may enter into and out of a slot 1715 that is proximal to the implant body, and the distal end of the support sheath 1702 may extend just proximal to where the protection wire 1714 exits said slot 1715 to extend off of the carrier sheath 1707 to cover the implant body 101. Such a position of the distal end of support sheath 1702 may provide a smooth transition over the weld ring as well as help maintain the relative position of the protection wire 1714 during delivery. The tip of the support sheath 1702 may be shaped to ensure smooth transitions and prevent damage to vasculature during delivery. Various features of the delivery system may be radioopaque, such as the distal tip of the carrier sheath 1707, the distal tip of the support sheath 1702, and the weld ring 1716.

FIG. 18 shows a perspective view of an embodiment of the distal end of the torque sheath 1813. Attached to the torque sheath is weld ring 1816. The inner lumen of the weld ring 1816 may be shaped with a specific geometric configuration to enable weld ring 1816 to be locked to carrier sheath 1807 (not shown in this image) to prevent relative rotation but interlock in such a way with carrier sheath 1807 to allow relative translation. A proximal end of protection wire 1814 and a right anchor release wire 1817 and left anchor release wire 1812 may be welded to weld ring 1816. Other attachment means of release and protection mechanisms may be possible. In one embodiment, the proximal ends of wires 1814, 1817, and 1812 are welded to the exterior surface of weld ring 1816. In one embodiment, the distal end of torque sheath 1813 extends over the exterior of weld ring 1816 to facilitate a robust bond of torque sheath 1813 to weld ring 1816 and further support the attachment of wires 1814, 1817, and 1812 to weld ring 1816. With the protection wire 1814 and anchor release wires 1812 and 1817 attached to torque sheath 1813, the relative motion of torque sheath 1813 proximal to carrier sheath 1807 may serve to disengage protection wire 1814 and anchor release wires 1814, 1812, and 1817 from carrier sheath 1807. It may be advantageous to design protection wire 1814 and anchor release wires 1812 and 1817 to be of short length, as longer wires may be more susceptible to stretching under tension when the wires are pulled to release. Friction of longer length wires may also result in a difficult release of the wires from the carrier sheath 1807. In another embodiment, protection wire 1814 and anchor release wires 1812 and 1817 may not attach to torque sheath 1813 but may instead extend proximally to a handle end where manipulation of wires directly may occur. In one embodiment, protection wire 1814 and anchor release wires 1812 and 1817 may be one wire.

Figure 19:
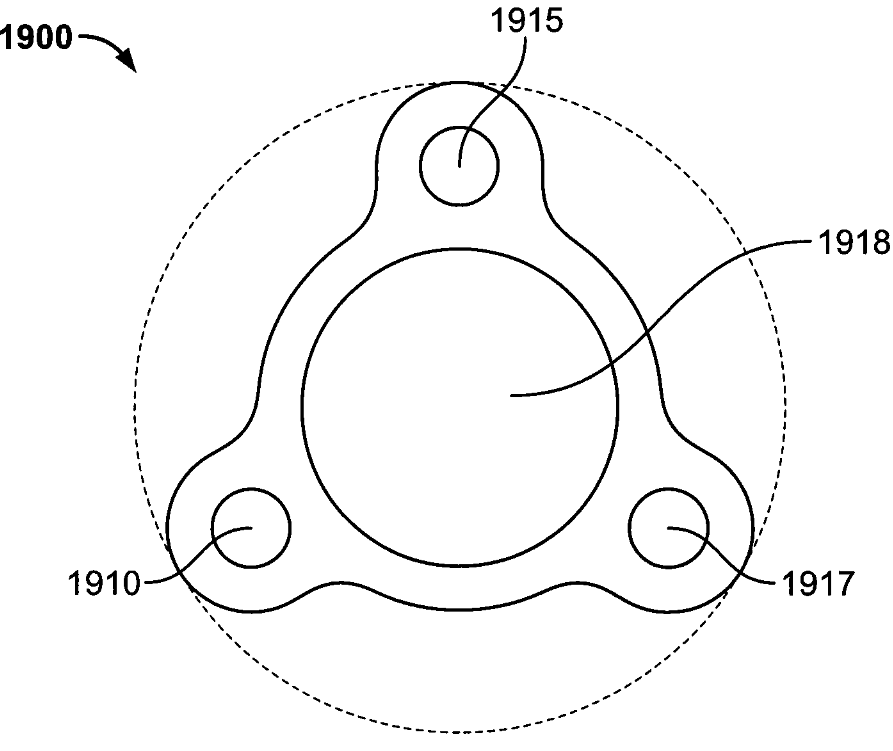
FIG. 19 shows a distal section of one embodiment of the carrier sheath.
Figure 20:
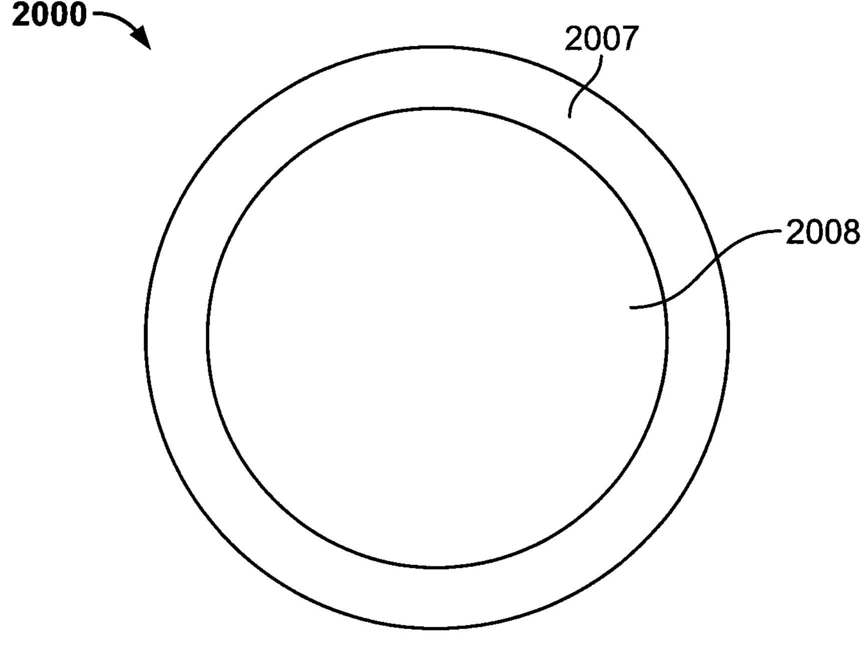
FIG. 20 shows a proximal section of one embodiment of the carrier sheath.

FIGS. 19 and 20 show features of one embodiment of a carrier sheath 2007. A multi lumen sheath section 1900 may be attached to a proximal section of carrier sheath 2007. In one embodiment, carrier sheath 2007 may have a distal cross section of multi lumen sheath section 1900 and a proximal cross section of a single lumen 2008. In one embodiment, carrier sheath 2007 is comprised of a sheath with a single lumen 2008 from the distal tip of the carrier sheath 2007 to the proximal tip of the carrier sheath 2007. In one embodiment, a multi lumen sheath section 1900 has a length of 2 cm, 3 cm, 5 cm, 10 cm, 90 cm, 110 cm, or 120 cm or another suitable length. In one embodiment, the multi lumen sheath section 1900 has a length approximately two to three times the length of the implant body 101. Multi-lumen sheath section 1900 may be symmetric such that lumens 1912, 1915, and 1917 are interchangeable. In one embodiment, lumen 1915 may be stripped off along a particular length to allow the implant body 101 to be secured close to the center axis of the core lumen 1918. This may be desirable to decrease the overall cross sectional profile of the implant body 101 sitting on top of the multi lumen sheath section 1900. The protection wire 1914 (not shown) may go in and out of slots on lumen 1915 to secure implant body 101 to multi lumen sheath section 1900. The anchor release wires 1912 and 1911 (not shown) may go in and out of slots on lumens 1910 and 1917 to secure the implant anchors in a collapsed position during delivery. Central lumen 1918 may be sized to accept carrier sheath 2007. A distal section of carrier sheath 2007 may be inserted through central lumen 1918 and bonded to central lumen 1918 via various means known in the art. Carrier sheath 2007 may have a central lumen 2008 to facilitate passage of a guidewire. Such a construction of carrier sheath 2007 with a distal portion comprising a multi-lumen sheath section could facilitate short protection and anchor release wires attached to a torque sheath, as described in FIGS. 16-18. In another embodiment, carrier sheath 2007 may have a cross section of multi lumen sheath section 1900 continuously from a distal end to a proximal end of carrier sheath 2007. In another embodiment, carrier sheath 2007 may have a cross section of a single lumen as shown in FIG. 20 continuously from a distal end to a proximal end of carrier sheath 2007.

The delivery system so described, or various related embodiments, may be used to deliver an implant to a target location, such as a distal lobe of the pulmonary artery.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof.

Having thus described the invention, we claim:

1. A method of deploying an implant to a target location comprising:

inserting a guide wire through a vasculature to a target location;

advancing a catheter delivery assembly from an insertion site, over said guide wire to said target location;

said catheter delivery assembly comprising:

an implant comprising at least one anchor;

a carrier sheath and a support sheath wherein said carrier sheath is positioned at least partially within said support sheath and, wherein, prior to deployment, said implant is positioned directly on an exterior of said carrier sheath while said carrier sheath is positioned at least partially within said support sheath; and one or more wires engage a portion of said at least one anchor in a collapsed configuration along said carrier sheath, which secure said implant to said carrier sheath, wherein said carrier sheath comprises at least one lumen extending along its length and a plurality of slots located distally and proximally relative to the implant, wherein said one or more wires pass into and out of the lumen through said slots to engage the anchor and hold the anchor in the collapsed configuration and wherein said one or more wires is configured to be at least partially retracted and disengaged from said at least one anchor to deploy said at least one anchor from said collapsed configuration;

moving said carrier sheath independent from and with respect to said support sheath to position said implant to a desired position;

deploying said at least one anchor from said collapsed configuration by retracting said one or more wires through said support sheath and releasing said implant from said carrier sheath.

2. The method of claim 1 further comprising injecting contrast through a lumen within at least one of said carrier sheath and said support sheath to allow visualization of the implant.

3. The method of claim 2 further comprising the step of injecting contrast through said lumen before said deploying step.

4. The method of claim 3 further comprising the step of conducting a calibration and orientation check of said implant to identify said desired position.

5. The method of claim 1 wherein said at least one anchor includes a proximal anchor that extends from a proximal end portion of said implant and a distal anchor that extends from a distal end portion of said implant, said proximal anchor extends opposite from said distal anchor.

6. The method of claim 5, wherein the step of deploying said implant includes partially retracting said one or more wires to deploy said distal anchor from said collapsed configuration while said proximal anchor remains collapsed.

7. The method of claim 6 further comprising the step of rotating said implant to a desired orientation after said distal anchor has been deployed.

8. The method of claim 6 further comprising the step of retracting said one or more wires to deploy said proximal anchor from said collapsed configuration.

9. The method of claim 6, wherein deployment comprises retracting the wires proximally through the lumen and the support sheath to disengage the anchor.

* * * * *